(12) United States Patent
Buttermann

(10) Patent No.: US 9,204,908 B2
(45) Date of Patent: Dec. 8, 2015

(54) SEGMENTAL ORTHOPEDIC DEVICE FOR SPINAL ELONGATION AND FOR TREATMENT OF SCOLIOSIS

(75) Inventor: Glenn R. Buttermann, Mahtomedi, MN (US)

(73) Assignee: Dynamic Spine, LLC, Mahtomedi, MN (US)

( * ) Notice: Subject to any disclaimer, the term of this patent is extended or adjusted under 35 U.S.C. 154(b) by 216 days.

(21) Appl. No.: 13/028,161

(22) Filed: Feb. 15, 2011

(65) Prior Publication Data
US 2011/0137353 A1 Jun. 9, 2011

Related U.S. Application Data

(63) Continuation-in-part of application No. 12/149,403, filed on Apr. 30, 2008, now Pat. No. 8,790,380.

(60) Provisional application No. 60/935,098, filed on Jul. 26, 2007.

(51) Int. Cl.
*A61B 17/70* (2006.01)
*A61B 17/66* (2006.01)

(52) U.S. Cl.
CPC .............. *A61B 17/707* (2013.01); *A61B 17/66* (2013.01); *A61B 17/7001* (2013.01); *A61B 17/7047* (2013.01)

(58) Field of Classification Search
CPC ............. A61B 17/688; A61B 17/7002; A61B 17/7032; A61B 17/7037; A61B 17/823; A61B 17/842; A61B 17/8076
USPC ........ 606/60, 75, 246–278, 300–324; 24/502, 24/514, 569; 403/60, 67–73, 77–79, 403/150–159, 161, 164, 165, 373, 403/374.1–374.4; 269/143, 249, 95; 29/276, 257
See application file for complete search history.

(56) References Cited

U.S. PATENT DOCUMENTS

| | | | | |
|---|---|---|---|---|
| 945,213 A | * | 1/1910 | Blackburn | 248/217.2 |
| 1,766,546 A | * | 6/1930 | Roos | 33/558.1 |

(Continued)

FOREIGN PATENT DOCUMENTS

| | | |
|---|---|---|
| DE | 28 21 678 A1 | 11/1979 |
| FR | 2782911 A | 3/2000 |

(Continued)

OTHER PUBLICATIONS

European Office Action dated Oct. 25, 2011 as received in corresponding European Patent Application No. 08743411.4, 5 pages.

(Continued)

*Primary Examiner* — Eduardo C Robert
*Assistant Examiner* — Michelle C Eckman
(74) *Attorney, Agent, or Firm* — Foley & Lardner LLP

(57) ABSTRACT

An orthopaedic device to realign bone segments comprises first and second attachment members and a strut or spacer member. The first attachment member is attached to a first rib bone or first transverse process or first lamina of a vertebra. The second attachment member is attached to a second rib bone or second transverse process or second lamina of a vertebra. The strut is positioned between the first and second attachment members. The strut is fixedly or releasably connected to the first and second attachment members to couple the first attachment member to the second attachment member. The strut provides distraction between the first and second rib bones or transverse processes to realign the rib bones. The attachment members comprise a clamp and screw combination.

34 Claims, 20 Drawing Sheets

(56) References Cited

U.S. PATENT DOCUMENTS

| | | | |
|---|---|---|---|
| 2,537,322 A * | 1/1951 | Wanzenberg | 73/859 |
| 2,543,550 A * | 2/1951 | Kneeland | 193/38 |
| 2,589,520 A * | 3/1952 | Wallenius | 248/177.1 |
| 2,722,440 A * | 11/1955 | Barton | 403/385 |
| 2,824,913 A * | 2/1958 | Taylor | 191/43 |
| 4,085,744 A | 4/1978 | Lewis et al. | |
| 4,361,141 A | 11/1982 | Tanner | |
| 4,364,381 A * | 12/1982 | Sher et al. | 606/96 |
| 4,409,968 A | 10/1983 | Drummond | |
| 4,411,259 A | 10/1983 | Drummond | |
| 4,422,451 A | 12/1983 | Kalamchi | |
| 4,531,522 A * | 7/1985 | Bedi et al. | 606/220 |
| 4,611,582 A * | 9/1986 | Duff | 606/258 |
| 4,619,447 A | 10/1986 | Blake | |
| 4,702,447 A * | 10/1987 | Westwood, III | 248/231.51 |
| 4,823,636 A * | 4/1989 | Suska | 24/569 |
| 4,852,841 A * | 8/1989 | Sebring | 248/231.31 |
| 4,901,964 A * | 2/1990 | McConnell | 248/231.51 |
| 4,950,270 A | 8/1990 | Bowman et al. | |
| 5,007,909 A | 4/1991 | Rogozinski | |
| 5,030,235 A | 7/1991 | Campbell, Jr. | |
| 5,074,864 A | 12/1991 | Cozad et al. | |
| 5,096,150 A * | 3/1992 | Westwood | 248/231.51 |
| 5,112,332 A | 5/1992 | Cozad et al. | |
| 5,116,334 A * | 5/1992 | Cozad et al. | 606/250 |
| 5,147,359 A * | 9/1992 | Cozad et al. | 606/276 |
| 5,190,543 A | 3/1993 | Schlapfer | |
| 5,261,908 A * | 11/1993 | Campbell, Jr. | 606/279 |
| 5,290,289 A * | 3/1994 | Sanders et al. | 606/279 |
| 5,330,472 A | 7/1994 | Metz-Stavenhagen | |
| 5,334,203 A | 8/1994 | Wagner | |
| 5,344,422 A | 9/1994 | Frigg | |
| 5,352,225 A | 10/1994 | Yuan et al. | |
| 5,380,326 A | 1/1995 | Lin | |
| 5,413,576 A * | 5/1995 | Rivard | 606/250 |
| 5,415,659 A * | 5/1995 | Lee et al. | 606/276 |
| 5,423,857 A * | 6/1995 | Rosenman et al. | 606/219 |
| 5,507,747 A * | 4/1996 | Yuan et al. | 606/276 |
| 5,520,689 A | 5/1996 | Schlapfer et al. | |
| 5,586,983 A * | 12/1996 | Sanders et al. | 606/277 |
| 5,630,816 A | 5/1997 | Kambin | |
| 5,632,744 A | 5/1997 | Campbell, Jr. | |
| 5,662,648 A * | 9/1997 | Faccioli et al. | 606/54 |
| 5,676,665 A * | 10/1997 | Bryan | 606/252 |
| 5,688,273 A | 11/1997 | Errico et al. | |
| 5,688,274 A | 11/1997 | Errico et al. | |
| 5,689,864 A * | 11/1997 | White | 24/514 |
| 5,697,650 A * | 12/1997 | Brown | 285/197 |
| 5,733,284 A | 3/1998 | Martin | |
| 5,800,548 A | 9/1998 | Martin et al. | |
| 6,053,917 A | 4/2000 | Sherman et al. | |
| 6,136,000 A * | 10/2000 | Louis et al. | 606/250 |
| 6,352,537 B1 * | 3/2002 | Strnad | 606/276 |
| 6,375,656 B1 * | 4/2002 | Faure | 606/279 |
| 6,387,097 B1 * | 5/2002 | Alby | 606/277 |
| 6,547,789 B1 * | 4/2003 | Ventre et al. | 606/308 |
| 6,589,243 B1 * | 7/2003 | Viart et al. | 606/250 |
| 6,626,909 B2 | 9/2003 | Chin | |
| 6,660,007 B2 * | 12/2003 | Khanna | 606/284 |
| 6,719,795 B1 * | 4/2004 | Cornwall et al. | 623/17.11 |
| 6,860,884 B2 * | 3/2005 | Shirado et al. | 606/330 |
| 6,926,242 B2 * | 8/2005 | Hall | 248/230.4 |
| 7,011,659 B2 * | 3/2006 | Lewis et al. | 606/276 |
| 7,029,472 B1 * | 4/2006 | Fortin | 606/60 |
| 7,137,986 B2 * | 11/2006 | Troxell et al. | 606/252 |
| 7,249,399 B2 | 7/2007 | Taylor | |
| 7,264,620 B2 * | 9/2007 | Taylor | 606/86 A |
| 7,338,490 B2 * | 3/2008 | Ogilvie et al. | 606/276 |
| 7,614,173 B2 * | 11/2009 | Kim | 40/612 |
| 7,635,365 B2 * | 12/2009 | Ellis et al. | 606/71 |
| 7,666,210 B2 | 2/2010 | Franck et al. | |
| 7,695,501 B2 * | 4/2010 | Ellis et al. | 606/281 |
| 7,703,358 B2 * | 4/2010 | Ubinana Felix | 81/487 |
| 7,713,284 B2 * | 5/2010 | Crofford | 606/219 |
| 7,717,938 B2 * | 5/2010 | Kim et al. | 606/250 |
| 7,883,532 B2 * | 2/2011 | Biscup et al. | 606/324 |
| 7,901,436 B2 * | 3/2011 | Baccelli | 606/272 |
| 7,922,746 B2 * | 4/2011 | Miller | 606/250 |
| 7,927,355 B2 * | 4/2011 | Berrevoets et al. | 606/250 |
| 7,927,357 B2 | 4/2011 | Sacher et al. | |
| 7,942,908 B2 | 5/2011 | Sacher et al. | |
| 7,966,703 B2 * | 6/2011 | Ubinana Felix | 24/514 |
| 7,980,521 B2 * | 7/2011 | Harr et al. | 248/229.1 |
| 8,025,678 B2 * | 9/2011 | Reynolds et al. | 606/249 |
| 8,025,683 B2 * | 9/2011 | Morrison | 606/278 |
| 8,043,337 B2 * | 10/2011 | Klyce et al. | 606/252 |
| 8,048,166 B2 * | 11/2011 | Brown et al. | 623/22.21 |
| 8,051,515 B1 * | 11/2011 | Kring | 5/658 |
| 8,057,472 B2 * | 11/2011 | Walker et al. | 606/57 |
| 8,075,597 B2 * | 12/2011 | Stahurski et al. | 606/260 |
| 8,080,037 B2 * | 12/2011 | Butler et al. | 606/250 |
| 8,080,046 B2 * | 12/2011 | Suddaby | 606/324 |
| 8,083,780 B2 * | 12/2011 | McClellan et al. | 606/279 |
| 8,105,366 B2 * | 1/2012 | Null et al. | 606/280 |
| 8,172,875 B2 * | 5/2012 | Taylor | 606/246 |
| 8,172,882 B2 * | 5/2012 | Klyce et al. | 606/276 |
| 8,172,887 B2 * | 5/2012 | Gabele | 606/324 |
| 8,177,823 B2 * | 5/2012 | Lake et al. | 606/330 |
| 8,197,515 B2 | 6/2012 | Levy et al. | |
| 8,197,543 B2 * | 6/2012 | Wang | 623/17.11 |
| 8,226,689 B2 * | 7/2012 | Jones et al. | 606/250 |
| 8,231,655 B2 * | 7/2012 | Stinson et al. | 606/247 |
| 8,241,334 B2 * | 8/2012 | Butler et al. | 606/278 |
| 8,246,660 B2 * | 8/2012 | Boris et al. | 606/280 |
| 8,292,924 B2 * | 10/2012 | Neary et al. | 606/250 |
| 8,298,275 B2 | 10/2012 | Rezach | |
| 8,313,514 B2 * | 11/2012 | Puno | 606/250 |
| 8,430,917 B2 | 4/2013 | Rezach | |
| 8,790,380 B2 | 7/2014 | Buttermann | |
| 8,915,962 B1 | 12/2014 | Suddaby | |
| 2002/0013585 A1 | 1/2002 | Gournay et al. | |
| 2002/0019633 A1 | 2/2002 | Ray | |
| 2002/0095156 A1 * | 7/2002 | Kuras et al. | 606/72 |
| 2002/0169451 A1 * | 11/2002 | Yeh | 606/61 |
| 2003/0004511 A1 * | 1/2003 | Ferree | 606/61 |
| 2003/0032959 A1 * | 2/2003 | Yeh | 606/61 |
| 2003/0045876 A1 | 3/2003 | Stahurski | |
| 2003/0080267 A1 * | 5/2003 | Eslick | 248/229.1 |
| 2003/0083659 A1 * | 5/2003 | Lin et al. | 606/61 |
| 2003/0088251 A1 | 5/2003 | Braun et al. | |
| 2003/0109881 A1 * | 6/2003 | Shirado et al. | 606/61 |
| 2003/0109882 A1 * | 6/2003 | Shirado et al. | 606/61 |
| 2003/0125738 A1 * | 7/2003 | Khanna | 606/61 |
| 2003/0125740 A1 * | 7/2003 | Khanna | 606/61 |
| 2003/0130659 A1 | 7/2003 | Haider | |
| 2003/0187437 A1 | 10/2003 | Ginsburg | |
| 2004/0030388 A1 * | 2/2004 | Null et al. | 623/17.11 |
| 2004/0055429 A1 * | 3/2004 | Winkler | 81/367 |
| 2004/0064140 A1 * | 4/2004 | Taylor et al. | 606/61 |
| 2004/0087948 A1 * | 5/2004 | Suddaby | 606/61 |
| 2004/0111091 A1 * | 6/2004 | Ogilvie et al. | 606/73 |
| 2004/0186472 A1 | 9/2004 | Lewis et al. | |
| 2005/0131412 A1 * | 6/2005 | Olevsky et al. | 606/69 |
| 2005/0171539 A1 | 8/2005 | Braun et al. | |
| 2005/0228377 A1 * | 10/2005 | Chao et al. | 606/61 |
| 2005/0251138 A1 * | 11/2005 | Boris et al. | 606/61 |
| 2005/0267475 A1 * | 12/2005 | Miller, III | 606/69 |
| 2005/0267480 A1 * | 12/2005 | Suddaby | 606/75 |
| 2005/0273100 A1 * | 12/2005 | Taylor | 606/61 |
| 2006/0036241 A1 * | 2/2006 | Siegal | 606/61 |
| 2006/0058790 A1 | 3/2006 | Carl et al. | |
| 2006/0084990 A1 * | 4/2006 | Gournay et al. | 606/61 |
| 2006/0116687 A1 | 6/2006 | Miller et al. | |
| 2006/0155279 A1 | 7/2006 | Ogilvie | |
| 2006/0229615 A1 * | 10/2006 | Abdou | 606/61 |
| 2006/0229616 A1 | 10/2006 | Albert et al. | |
| 2006/0235391 A1 * | 10/2006 | Sutterlin | 606/61 |
| 2006/0241601 A1 * | 10/2006 | Trautwein et al. | 606/61 |
| 2006/0247626 A1 | 11/2006 | Taylor et al. | |
| 2006/0271193 A1 | 11/2006 | Hartmann et al. | |
| 2006/0293663 A1 * | 12/2006 | Walkenhorst et al. | 606/61 |
| 2007/0016189 A1 * | 1/2007 | Lake et al. | 606/61 |
| 2007/0072459 A1 | 3/2007 | Stahurski et al. | |
| 2007/0083201 A1 * | 4/2007 | Jones et al. | 606/61 |

(56) References Cited

U.S. PATENT DOCUMENTS

| | | |
|---|---|---|
| 2007/0118118 A1 | 5/2007 | Kwak et al. |
| 2007/0123883 A1* | 5/2007 | Ellis et al. ............ 606/69 |
| 2007/0225713 A1 | 9/2007 | Altarac et al. |
| 2007/0239161 A1 | 10/2007 | Giger et al. |
| 2007/0276384 A1 | 11/2007 | Spratt |
| 2008/0033436 A1* | 2/2008 | Song et al. ............ 606/61 |
| 2008/0077144 A1* | 3/2008 | Crofford ................ 606/75 |
| 2008/0103512 A1* | 5/2008 | Gately ................. 606/151 |
| 2008/0114401 A1* | 5/2008 | Liu et al. ............. 606/276 |
| 2008/0177315 A1 | 7/2008 | Usher |
| 2008/0228225 A1* | 9/2008 | Trautwein et al. .... 606/246 |
| 2008/0234733 A1* | 9/2008 | Scrantz et al. ....... 606/246 |
| 2008/0234766 A1 | 9/2008 | Henderson et al. |
| 2008/0294200 A1* | 11/2008 | Kohm et al. ......... 606/279 |
| 2008/0306551 A1* | 12/2008 | Sanders et al. ...... 606/301 |
| 2009/0018584 A1 | 1/2009 | Henderson et al. |
| 2009/0030457 A1 | 1/2009 | Janowski et al. |
| 2009/0030462 A1 | 1/2009 | Buttermann |
| 2009/0062869 A1* | 3/2009 | Claverie et al. ...... 606/324 |
| 2009/0105766 A1 | 4/2009 | Thompson et al. |
| 2009/0112263 A1 | 4/2009 | Pool et al. |
| 2009/0118774 A1* | 5/2009 | Miller, III ........... 606/324 |
| 2009/0118775 A1* | 5/2009 | Burke ................. 606/324 |
| 2009/0163920 A1* | 6/2009 | Hochschuler et al. ... 606/74 |
| 2009/0177230 A1 | 7/2009 | Henderson et al. |
| 2009/0198277 A1* | 8/2009 | Gordon et al. ....... 606/248 |
| 2009/0248090 A1 | 10/2009 | Gordon et al. |
| 2009/0270929 A1* | 10/2009 | Suddaby .............. 606/324 |
| 2009/0287253 A1* | 11/2009 | Felix et al. .......... 606/278 |
| 2010/0057127 A1* | 3/2010 | McGuire et al. ..... 606/246 |
| 2010/0069960 A1* | 3/2010 | Chaput ................ 606/249 |
| 2010/0094303 A1 | 4/2010 | Chang et al. |
| 2010/0121381 A1* | 5/2010 | Berta et al. .......... 606/264 |
| 2010/0137913 A1 | 6/2010 | Khatchadourian et al. |
| 2010/0152575 A1 | 6/2010 | Henderson et al. |
| 2010/0160979 A1* | 6/2010 | Tornier ................ 606/305 |
| 2010/0179597 A1 | 7/2010 | Henderson et al. |
| 2010/0198274 A1* | 8/2010 | Yeung et al. ......... 606/86 A |
| 2010/0217271 A1 | 8/2010 | Pool et al. |
| 2010/0222822 A1 | 9/2010 | Farris et al. |
| 2010/0241230 A1* | 9/2010 | Mazzuca et al. ...... 623/17.11 |
| 2010/0249842 A1* | 9/2010 | Mir .................... 606/250 |
| 2010/0274291 A1 | 10/2010 | McClellan et al. |
| 2010/0292739 A1* | 11/2010 | Schwab ............... 606/305 |
| 2010/0305616 A1* | 12/2010 | Carbone .............. 606/264 |
| 2011/0106163 A1* | 5/2011 | Hochschuler et al. ..... 606/264 |
| 2011/0111929 A1* | 5/2011 | Allison et al. ....... 482/108 |
| 2011/0137353 A1 | 6/2011 | Buttermann |
| 2011/0144694 A1 | 6/2011 | Laeng et al. |
| 2011/0160779 A1 | 6/2011 | Schlaepfer et al. |
| 2011/0178552 A1 | 7/2011 | Biscup et al. |
| 2011/0184463 A1* | 7/2011 | Schwend .............. 606/258 |
| 2011/0251643 A1 | 10/2011 | Miladi |
| 2011/0257690 A1 | 10/2011 | Rezach |
| 2011/0288592 A1 | 11/2011 | McKinley |
| 2011/0313323 A1 | 12/2011 | Henderson et al. |
| 2012/0016420 A1* | 1/2012 | Naraghi ............... 606/250 |
| 2012/0035656 A1 | 2/2012 | Pool et al. |
| 2012/0035661 A1 | 2/2012 | Pool et al. |
| 2012/0047690 A1* | 3/2012 | Ginocchio ............ 24/132 WL |
| 2012/0083851 A1* | 4/2012 | Felix et al. .......... 606/305 |
| 2012/0088380 A1* | 4/2012 | Smith ................. 439/100 |
| 2012/0209328 A1* | 8/2012 | Alamin et al. ....... 606/248 |
| 2012/0271352 A1* | 10/2012 | Schulze et al. ...... 606/247 |
| 2012/0271354 A1* | 10/2012 | Baccelli et al. ...... 606/263 |
| 2012/0283780 A1* | 11/2012 | Ludwig et al. ....... 606/270 |
| 2013/0041410 A1 | 2/2013 | Hestad et al. |
| 2013/0046352 A1 | 2/2013 | McClintock |
| 2013/0131738 A1 | 5/2013 | Powell et al. |
| 2013/0184770 A1 | 7/2013 | Buttermann |
| 2013/0218208 A1 | 8/2013 | Khoury |
| 2013/0231704 A1 | 9/2013 | Larroque-Lahitette |
| 2013/0274807 A1 | 10/2013 | Prajapati |
| 2013/0304129 A1 | 11/2013 | Hawkins et al. |
| 2014/0135853 A1 | 5/2014 | Reisberg |
| 2014/0214087 A1 | 7/2014 | Wahl et al. |
| 2014/0222074 A1 | 8/2014 | Rathbun et al. |
| 2014/0236234 A1 | 8/2014 | Kroll et al. |
| 2014/0257488 A1 | 9/2014 | Alheidt et al. |
| 2014/0277147 A1 | 9/2014 | Alexander et al. |
| 2014/0336705 A1 | 11/2014 | Buttermann |
| 2014/0343612 A1 | 11/2014 | Rezach et al. |
| 2015/0025574 A1 | 1/2015 | Mackall |
| 2015/0032158 A1 | 1/2015 | Khajavi et al. |
| 2015/0032159 A1 | 1/2015 | Beger et al. |

FOREIGN PATENT DOCUMENTS

| | | |
|---|---|---|
| FR | 2892617 A | 5/2007 |
| WO | WO 90/12553 A | 11/1990 |
| WO | WO 93/25161 A | 12/1993 |
| WO | WO-97/29707 A | 8/1997 |
| WO | WO 2004/019757 A2 | 3/2004 |
| WO | WO 2005/044152 A1 | 5/2005 |
| WO | WO 2011/133690 A2 | 10/2011 |
| WO | WO-2011/156573 A1 | 12/2011 |

OTHER PUBLICATIONS

International Search Report mailed Nov. 12, 2008 in PCT/US2008/005532, 5 pages.
Kim, Won Joong, et al. "The Influence of Fixation Rigidity on Intervertebral Joints—An Experimental Comparison between a Rigid and a Flexible System", J Korean Neurosurg Soc, vol. 37, 2005, pp. 364-369.
US Office Action received in U.S. Appl. No. 12/149,403 dated Feb. 22, 2011.
International Search Report and Written Opinion dated Jun. 29, 2012 as received in corresponding PCT Application No. PCT/US2012/024887.
US Office Action dated Sep. 24, 2012 as received in corresponding U.S. Appl. No. 12/149,403.
European Office Action dated Sep. 23, 2010 as received in corresponding European Patent Application No. 08743411.4, 3 pages.
US Office Action dated Aug. 10, 2011 as received in corresponding U.S. Appl. No. 12/149,403, 12 pages.
International Search Report and Written Opinion dated Oct. 4, 2011 as received in corresponding PCT Application No. PCT/US2011/039760, 13 pages.
International Search Report and Written Opinion in PCT/US2013/027386 dated Apr. 26, 2013.
Patent Examination Report received in connection with related Australian application No. AU2008279798 dtd Nov. 14, 2012.
Australian Office Action dated Jan. 15, 2014 received in corresponding AU Application No. 2011264818.
US Notice of Allowance Dtd Mar. 14, 2014.
Supplementary European Search Report in corresponding European Application No. 11793147.7 dated Oct. 10, 2014, 7 pages.
Notice of Allowance in U.S. Appl. No. 13/702,854 dated Feb. 20, 2015.
US Office Action issued in U.S. Appl. No. 14/444,860 dated Mar. 12, 2015.
Patent Examination Report No. 2 received in corresponding Australian application No. 2011264818 dated Mar. 5, 2015, 4 pages.
Office Action issued in co-pending Canadian Application No. 2,694,437 mailed May 13, 2014.
Office Action issued in co-pending Canadian Patent Application No. 2,694,437 mailed Mar. 5, 2015.
Notice of Allowance dated Jun. 8, 2015, in U.S. Appl. No. 13/702,854, 9 pages.
Notice of Allowance dated Aug. 27, 2015, in U.S. Appl. No. 14/444,860, 13 pages.
Patent Examination Report No. 1 dated Aug. 6, 2015, recieved in corresponding Australian application No. 2012217924, 7 pages.

* cited by examiner

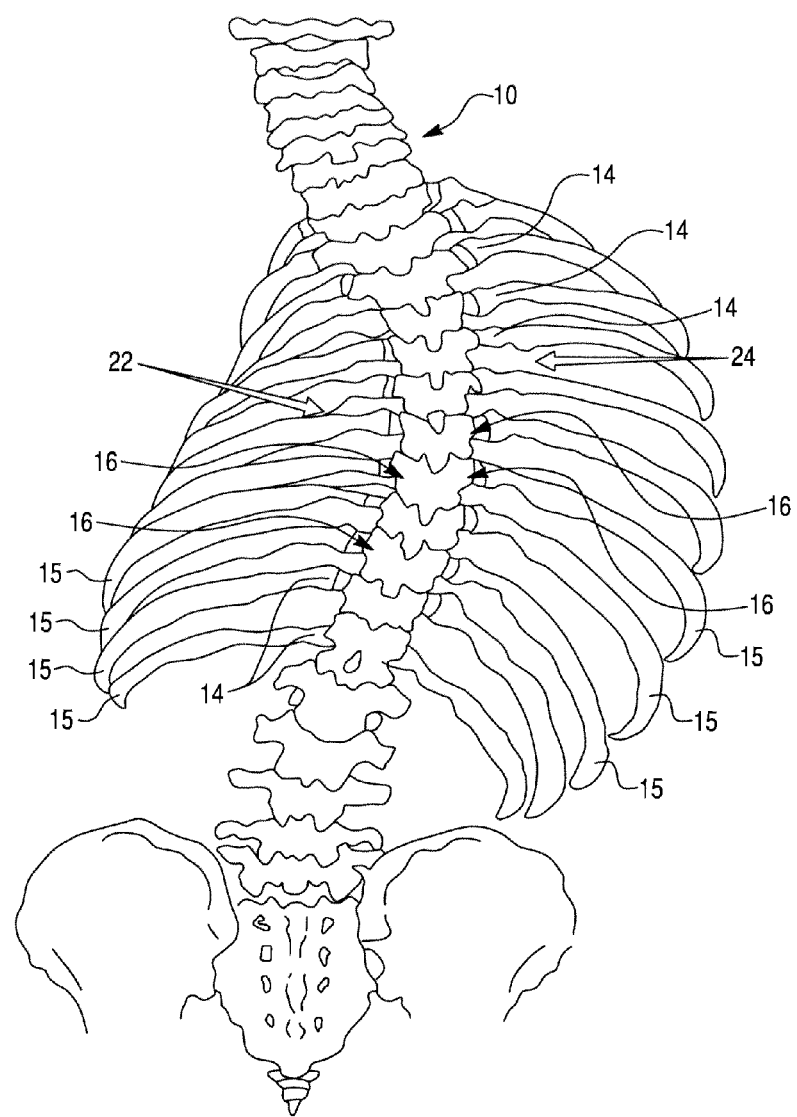

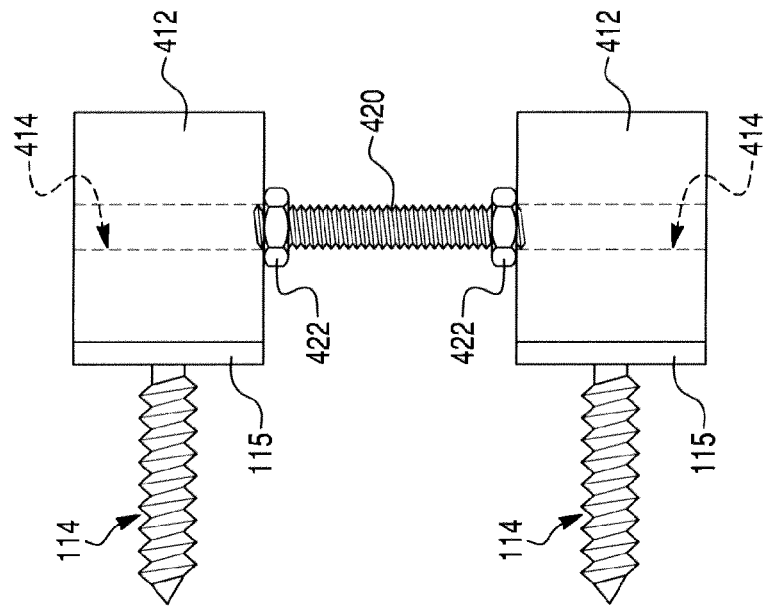
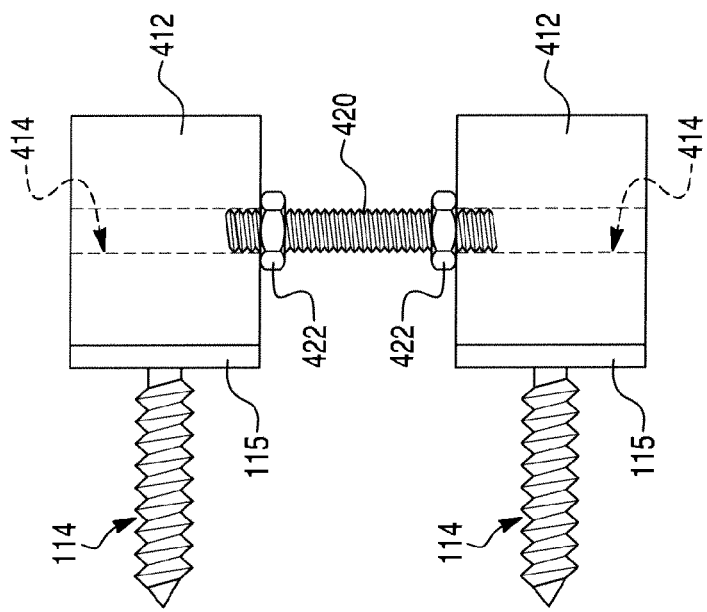

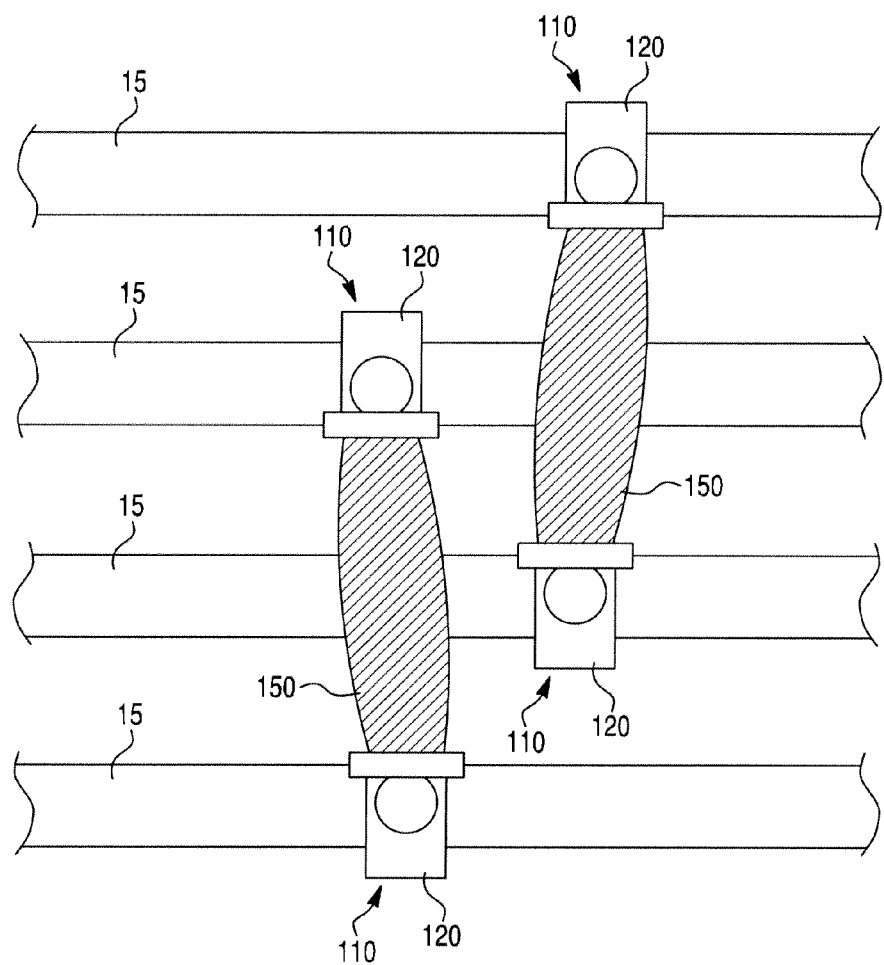

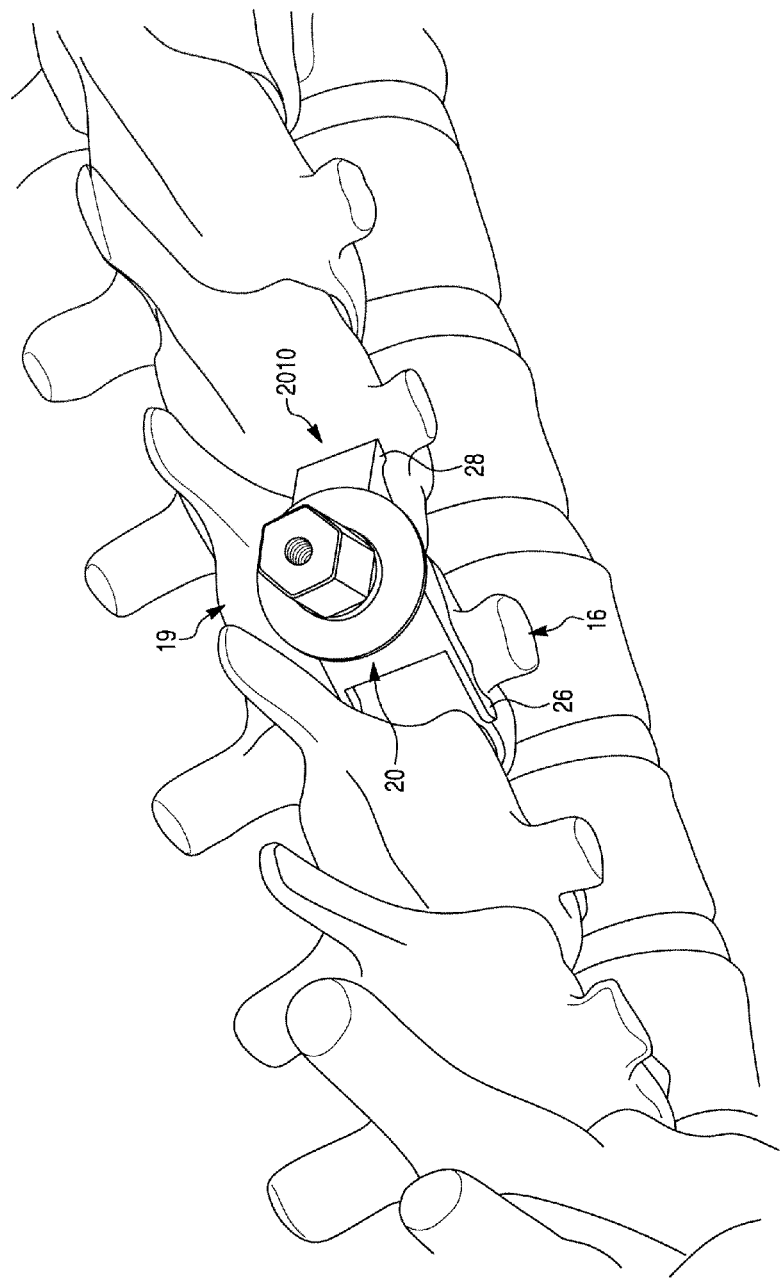

SEGMENTAL ORTHOPEDIC DEVICE FOR SPINAL ELONGATION AND FOR TREATMENT OF SCOLIOSIS

CROSS-REFERENCE TO RELATED PATENT APPLICATIONS

This application is a continuation-in-part of U.S. patent application Ser. No. 12/149,403 filed Apr. 30, 2008; which claims priority to U.S. Provisional Application No. 60/935, 098, filed Jul. 26, 2007; the disclosures of which are incorporated herein by reference in their entirety.

BACKGROUND OF THE INVENTION

The present disclosure relates generally to orthopaedic devices. The present disclosure relates to orthopaedic devices for spinal elongation and for treatment of scoliosis.

External and internal fixators that are anchored to segments of bone have been used extensively over the last century. The fixators may be rigid or dynamic, and they may be expandable or apply distractive/compressive forces (longitudinal or at an angle) to realign bone segments. Historically these devices were most often used for trauma cases to stabilize fractures. Modern applications have also used them for extremity deformity, limb lengthening, and bone transport.

Orthopaedic devices can be segmental or non-segmental. Non-segmental devices typically have bone anchors at the ends of the treatment areas, and segmental devices typically have bone anchors at each adjacent bone segment.

There is a need for a segmental orthopaedic implant for spinal elongation and for treatment of scoliosis (the abnormal side-to-side curvature of a spine). Fusion instrumentation for scoliosis often consists of hooks, rods and screws of which pedicle screws are common. Hooks and screws are typically placed adjacent to the spinal facet joints. Fusion results in a loss of spinal mobility, loss of spinal growth and may aggravate spinal disc degeneration.

SUMMARY OF THE INVENTION

One embodiment of the invention relates to an orthopaedic device to realign bone segments. The orthopaedic device comprises: a first attachment member configured to be attached to at least one of a first rib bone, first transverse process, and first lamina of a vertebra; a second attachment member configured to be attached to at least one of a second rib bone, second transverse process, and second lamina of a vertebra; and a strut positioned between the first and second attachment members arranged between vertebrae or within a vertebral segment. The strut is one of fixedly and releasably connected to the first and second attachment members to couple the first attachment member to the second attachment member.

Another embodiment of the invention relates to an orthopaedic device for realigning bone segments. The orthopaedic device comprises a first attachment member. The first attachment member includes a clamp, a screw and a projection. The clamp is configured to attach to at least one of a rib bone, a transverse process, and lamina of a vertebra. The clamp includes an upper arm, a lower arm, and a hinge. The screw is configured to be inserted into an opening in the clamp. The screw includes a screw head. The screw is configured to fix into the at least one of the rib bone, the transverse process, and the lamina of the vertebra to prevent rotational movement or sliding of the clamp along the at least one of the bone, the transverse process and the lamina of the vertebra. The projection is configured to receive a spacer member to connect the first attachment member to a second attachment member.

Another embodiment of the invention relates to an orthopaedic device for realigning bone segments. The orthopaedic device comprises an attachment member that includes a clamp and a screw. The clamp is configured to attach to at least one of a rib bone, transverse process and lamina of a vertebra. The clamp includes an upper clamp body, a lower clamp body, a plurality of clamp arms and a hinge. The screw is configured to be inserted into an opening in the clamp. The screw includes a screw head. The screw is configured to fix into the at least one of the rib bone, transverse process, and lamina to prevent rotational movement or sliding of the clamp along the at least one of bone, transverse process and lamina. The orthopaedic device comprises at least one of: (a) at least one of the clamp arms is asymmetrical to another of the clamp arms; and (b) the upper clamp body is asymmetrical to the lower clamp body.

Yet another embodiment of the invention relates to a method of attaching an orthopaedic device to at least one of a rib bone, transverse process and lamina of a vertebra. The orthopaedic device comprises a first attachment member that includes a clamp and a screw. The clamp includes an upper arm with a shoulder, a lower arm with a shoulder, and a hinge. The screw includes a screw head. The method comprises: (i) positioning the attachment member over the at least one of rib bone, transverse process and lamina of the vertebra to which the attachment member will be attached; (2) advancing the screw through an opening in the clamp so that the screw head engages the shoulders of the clamp to push the upper arm and lower arm to rotate toward each other; and (3) clamping the upper arm and the lower arm about the at least one of rib bone, transverse process and lamina of the vertebra.

It is to be understood that both the foregoing general description and the following detailed description are exemplary and explanatory only, and are not restrictive of the invention as claimed.

BRIEF DESCRIPTION OF THE DRAWINGS

Features, aspects, and advantages of embodiments of the present invention will become apparent from the following description, and the accompanying exemplary embodiments shown in the drawing, which is briefly described below.

FIG. 1(a) illustrates a concave aspect of a scoliotic spine.

FIG. 3(a) is a perspective view of an attachment member according to an embodiment. FIG. 3(b) illustrates a cross-sectional top view of the attachment member of FIG. 3(a) during attachment to a rib. FIG. 3(c) illustrates a cross-sectional side view of the attachment member of FIG. 3(a) prior to attachment to a rib. FIG. 3(d) illustrates a cross-sectional side view of the attachment member of FIG. 3(a) attached to a rib. FIG. 3(e) illustrates a front view of the attachment member of FIG. 3(a).

FIG. 4(a) is an exploded view of a clamp and screw prior to attachment to a cross-section of a rib in which a plate is attached to the screw and the clamp includes a wedge. FIG. 4(b) illustrates a side view of the attachment member of FIG. 4(a).

FIG. 7(a) illustrates an attachment member attached to a first rib and an attachment member attached to a second rib. FIG. 7(b) illustrates a spacer member attached to the attachment members of FIG. 7(a) in which the spacer member is in a shortened configuration. FIG. 7(c) illustrates a spacer member attached to the attachment members of FIG. 7(a) in which the spacer member is in a lengthened or expanded configuration.

FIG. 9(a) illustrates an orthopaedic device attached to adjacent ribs with a spacer member comprising a polymer matrix with a fabric housing attached to the attachment members according to an exemplary embodiment. FIG. 9(b) illustrates a perspective view of the fabric housing of FIG. 9(a).

FIGS. 10(a) and 10(b) illustrate screws of attachment members with a turnbuckle assembly according to another embodiment. FIG. 10(a) illustrates a threaded rod extending into passages of adjacent screws. FIG. 10(a) illustrates the threaded rod in a position different from FIG. 10(a).

FIG. 11 illustrates orthopaedic devices with attachment members with connecting spacer members attached at non-adjacent rib bones.

FIG. 30 illustrates a top view of an attachment member clamped onto the spine.

DETAILED DESCRIPTION OF THE PREFERRED EMBODIMENTS

Figure 1B:
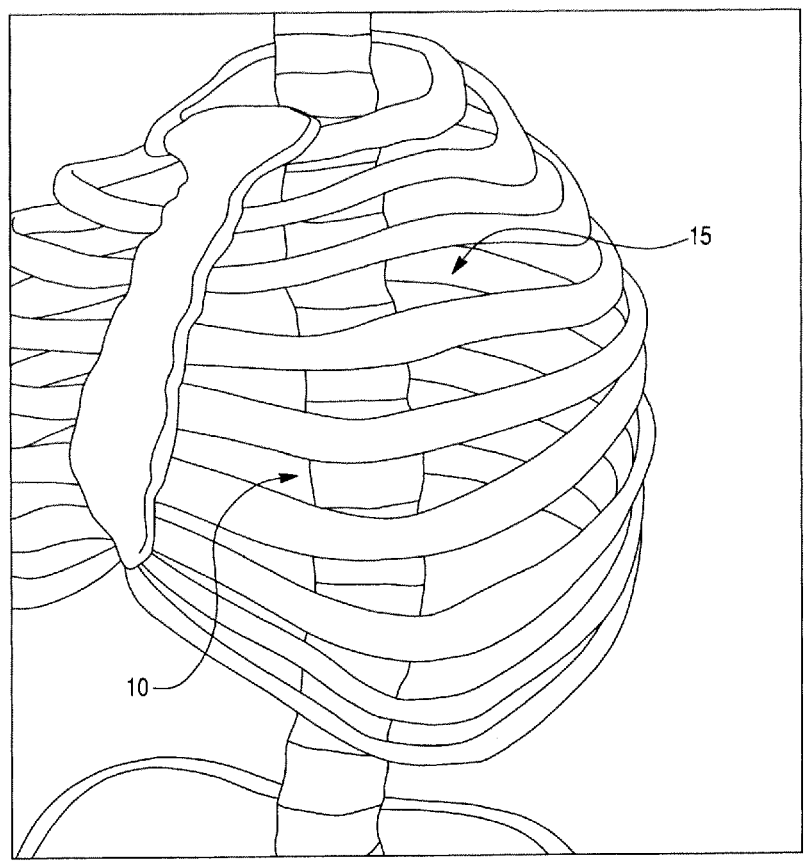
FIG. 1(b) illustrates an anterior oblique view of the spine.

The disclosure relates to an orthopaedic device to realign bone segments. The orthopaedic device can have multiple components, each including attachment members to attach to hone and a spacer member or a fixing rod (hereinafter referred to as a spacer member), a strut and/or a spacer member, that allow segmental realignment of bone. The orthopaedic device can be anchored to adjacent segments of hone by attachment members and may be expanded via the spacer member to realign the bone segments. The attachment members alternate with the spacer members as will be understood from the FIGURES. The spacer members also may allow bending within themselves or at the connection between the spacer members and the attachment members. The strut allows a horizontal connection between attachment members that are arranged between vertebra or within a vertebral segment so that a surgeon may lever and axially rotate the vertebra. For example, in scoliosis, vertebrae may be rotated axially from the normal orientation. Fixation of side by side attachment members that are connected by a strut provides secure fixation to the spine to allow for torsional correction of the rotated vertebra (such as by a derotation maneuver). The spacer member can fix the rotated or moved vertebral bodies (such as after rotation by a surgeon with the strut) into position by fixing an upper attachment member and a lower attachment member (i.e., spacer member fixes two attachment members in a generally vertical direction).

In an exemplary embodiment, the orthopaedic device 100 may be used to treat and correct scoliosis, which is the side-to-side or lateral curvature of the spine 10. The orthopaedic device 100 also may be used to correct other orthopaedic and/or spinal defects.

The orthopaedic device 100 can provide a fusionless treatment for patients with scoliosis. This orthopaedic device 100 can be fusionless in the sense that it can differ from current treatment for advanced scoliosis, which straightens the spine with rigid instrumentation (combination of hooks, screws, and rods) and then requires spinal fusion that eliminates all mobility between the vertebral segments with the fused region. The orthopaedic device 100, according to embodiments of the invention, allows mobility between segments of the spine 10.

Known fusionless devices, such as a tether or staples, are placed on the vertebral bodies at the convexity 24 of the scoliotic spine 10 and seek to correct a deformity by tethering and attempting to arrest or slow spinal growth at the convex aspect (side) 24 of the spine 10. In contrast, the orthopaedic device 100, according to embodiments of the present disclosure, is placed at the concavity 22 of the scoliotic spine 10. Correction of the scoliosis is achieved by elongation or movement of the orthopaedic device 100. This elongation is achieved by expansion or flexing of individual spacer (or expandable) members 150, and, according to an exemplary embodiment, such expansion occurs after all attachment members 110 and spacer members 150 are implanted.

Figure 2:
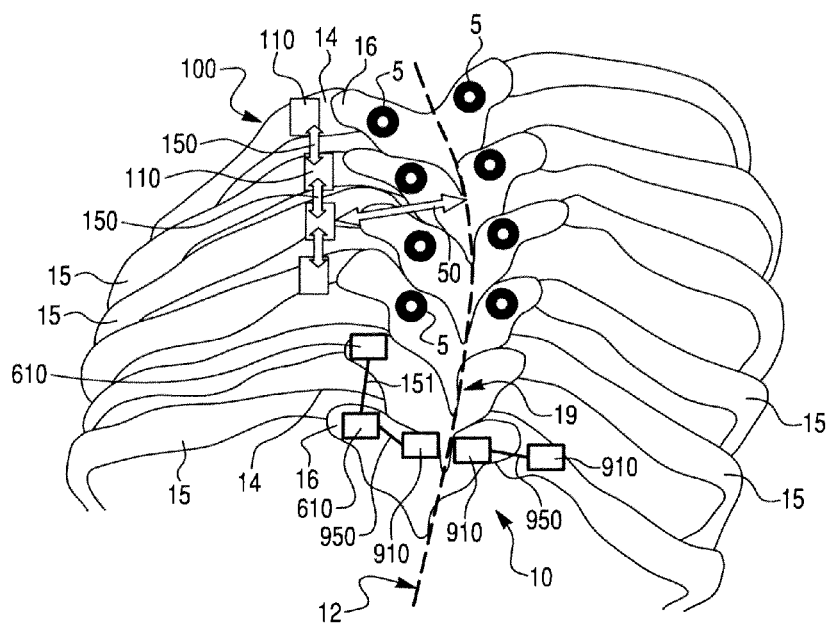
FIG. 2 illustrates a moment (or lever) arm that extends from a midline of the spine to an attachment member attached at a rib bone or transverse process or lamina, in which upper and lower attachment members are connected by a spacer member, and in which side-by-side attachment members are connected by a strut.
Figure 3A:
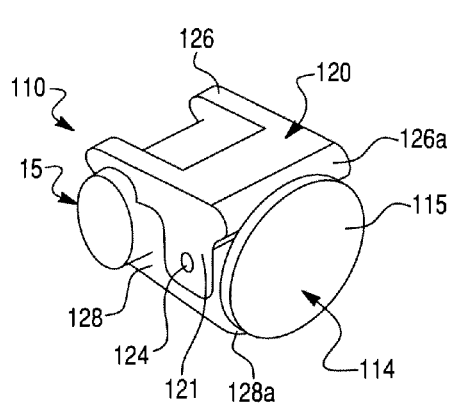
FIGS. 3(a)-3(e) illustrate an attachment member with a clamp/screw combination according to an exemplary embodiment.
Figure 3B:
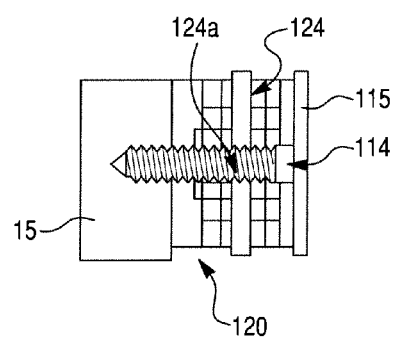
Figure 3C:
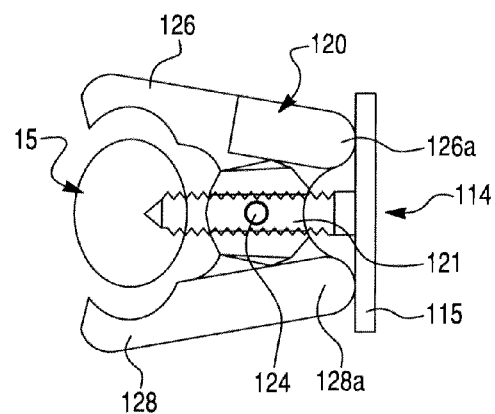
Figure 3D:
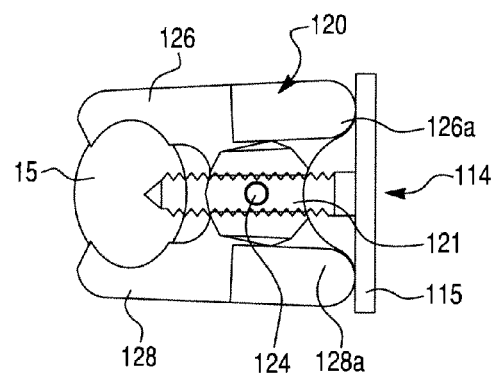
Figure 3E:
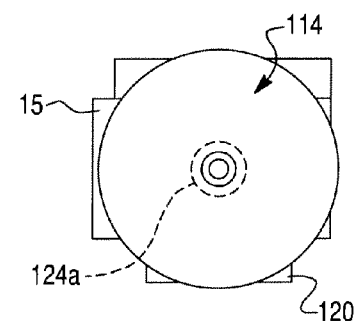

According to an exemplary embodiment, the orthopaedic device 100 attaches to a lateral concave aspect 22 of the spine 10 or proximal rib bone 15 (such as the rib head 14). Alternatively, the attachment members 110 are attached to a lamina 19 of a vertebra (FIG. 2). The orthopaedic device 100 elongates over time (such as from minutes to days); the device 100 remains in an elongated position after implantation; and the device 100 is not entirely rigid. The elongation time can vary depending upon the specific spacer member 150 utilized.

The orthopaedic device 100 comprises first and second attachment members 110 that are configured to be attached to adjacent rib bones 15 or transverse processes 16, and a spacer member 150 positioned between the first and second attachment members 110. The spacer member 150 provides distraction between the first and second rib bones 15 or transverse processes 16 to realign the rib bones and ultimately the spine 10. The spacer member 150 can be expandable and/or flexible. Alternatively, the spacer member 150 is fixed and does not expand. Alternatively, the attachment members 110 are attached to non-adjacent rib bones 15 or transverse processes 16.

Figure 29:
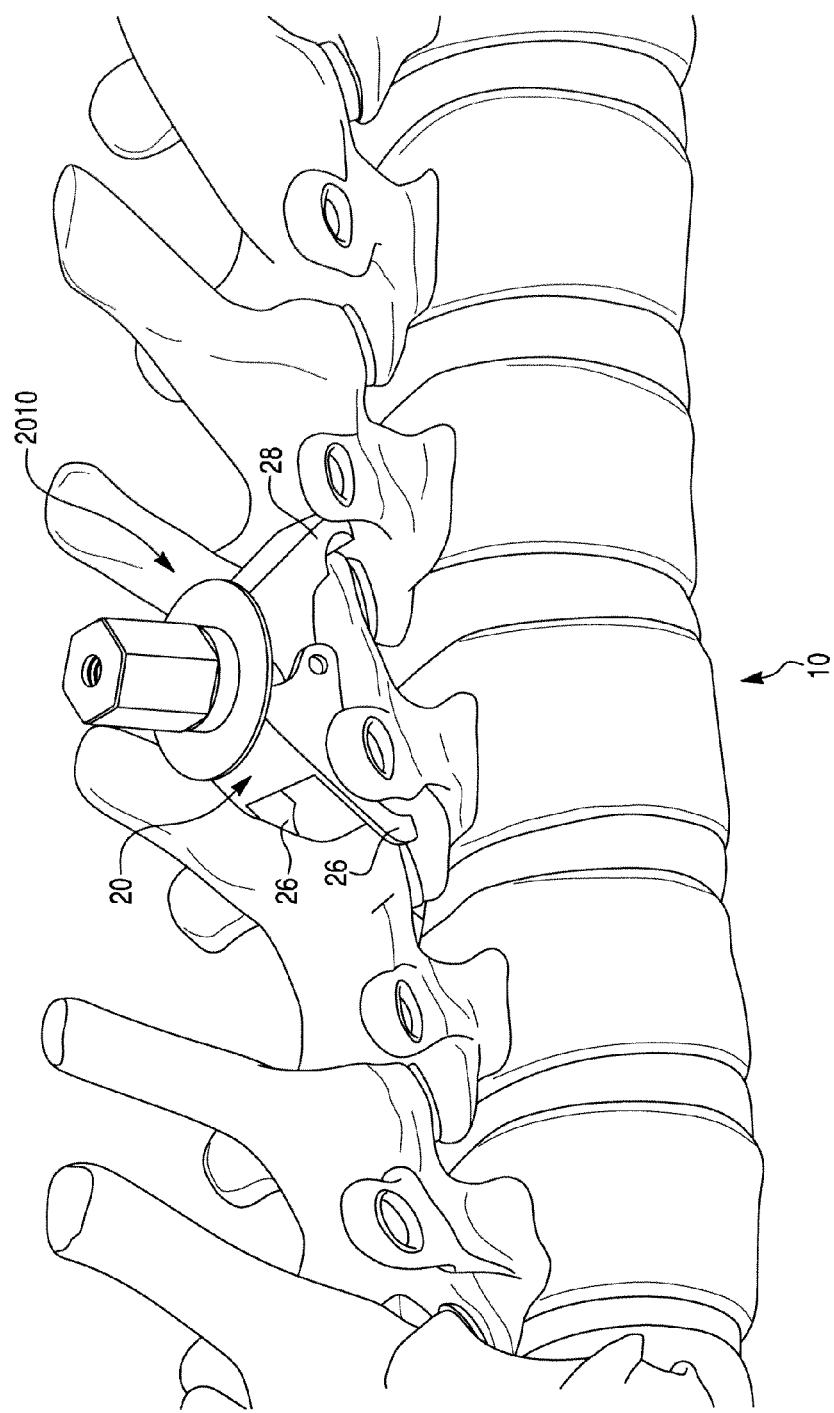
FIG. 29 illustrates a perspective view of an attachment member clamped onto the spine.

The attachment members 110 of the orthopaedic device 100 can be attached to the lateral aspect (lateral masses) of the spine 10 (such as to one of the transverse process 16, lamina 19, facet joint and caudal articular process) or proximal rib bone 15 just adjacent to the transverse process (such as near the rib head 14). FIGS. 29-30 show an attachment member 2010 attached to the lateral mass of the spine 10 with upper arms 26 and lower arms 28 of a clamp 20 gripping the lamina 19, transverse process 16 and caudal articular process. The attachment members 110 can attach to the transverse process 16 of the vertebrae, rib bones 15, other regions of the vertebrae or bones on the appendicular skeleton. The device 100 is attached to the concave aspect 22 of the scoliotic curve so that, when the spacer members 150 expand, a corrective force is applied and straightening of the scoliosis occurs. The concave aspect 22 of the spine 10 is the inner or concave portion of the curved spine 10, such as shown in FIG. 1. According to an exemplary embodiment, the orthopaedic device 100 has multiple attachments to bone.

According to an exemplary embodiment shown in FIG. 2, the orthopaedic device 100 is positioned laterally from a midline 12 of the spine 10 to produce greater mechanical advantage by having a longer lever arm 50 such that correction of the deformity may be easier. The orthopaedic device 100 can be attached to a transverse process (which is lateral to the midline 12 of a spine 10) or along a rib bone 15 (such as at a rib head 14 or along a middle portion of the rib bone 15). For example, the attachment members 110 are configured to be attached to a proximal or middle portion of the rib bone 15. FIG. 2 illustrates a moment (or lever) arm 50 to a rib bone 15 from the axis of rotation, which for a spinal segment is approximately the midline 12 of the spine 10 at the spinal disc. Leverage is increased by attaching the orthopaedic device 100 at a proximal portion or middle portion of the rib bone 15. Mechanically, a greater corrective bending moment is produced with the longer lever arm 50 for a given distraction force produced by the spacer member 150. In other words, the orthopaedic device 100 is preferably attached at a location that is lateral from the spinal vertebrae.

The spacer member 150, when positioned laterally from the spinal vertebrae, gives a longer lever arm 50 to move the rib bones 15 apart and correct the scoliotic curve of the spine 10. By having the attachment members 110 positioned laterally of the spine 10 (i.e., at a proximal or middle portion of the rib bones 15), a greater corrective force may be applied in the correction of the scoliotic spine.

In an exemplary embodiment, each spinal (or vertebral) level or segment has its own attachment member 110. Since the entire orthopaedic device 100 may be modular, the amount of expansion between each segment may be selected by the operating surgeon. The spacer members may be replaced without requiring removal of the associated attachment members. The spacer member 150 is releasably connected to the attachment members 110. The spacer member 150 is releasable because the spacer member 150 is configured to be removed from corresponding attachment members 110 while the corresponding attachment members remain in situ. The releasable connection is configured to allow for the spacer member 150 to be exchanged without requiring removal of corresponding attachment members 110. For example, the spacer member 150 can be removed without damaging the attachment members 110. A first spacer member 150 with a given force can be replaced with another spacer member 150 that provides a different corrective force. A spacer member 150 can also be exchanged for a different sized spacer member 150. For example, a shorter or longer spacer member 150 may be needed depending upon the current or desired spacing between rib bones 15.

According to an exemplary embodiment, the orthopaedic device 100 may be modular to allow for additional attachment members 110 and/or spacer members 150 to be placed or existing attachment members 110 and/or spacer members 150 to be exchanged for others of greater size for additional deformity correction. The attachment members 110 can be removed/released, for example, by unscrewing of the screw head 114.

In an exemplary embodiment, the orthopaedic device 100 may be modular in that its attachment 110 and/or spacer members 150 may be exchanged and/or replaced depending upon the needs of the patient. For example, if the desired spinal correction is not achieved or if additional correction is desired, the modular nature of the orthopaedic device 100 allows the surgeon to exchange spacer members 150 with different corrective forces and/or size either at the time of initial implantation or at a future date. By incrementally correcting the spinal deformity, or by staging the correction over multiple surgeries, the surgeon can minimize risk of spinal cord injury because the surgeon can avoid too much correction, with potential stretching of the spinal cord, in a single setting.

The screw 114 can be configured to connect to the rib bone 15, transverse process 16, lamina 19, caudal articular process or facet joint. The screw 114 can include a screw head 115. The attachment members 110 can also include a nail instead of a screw 114.

In an exemplary embodiment, the orthopaedic device 100 includes multiple attachments to bone via a plurality of attachment members 110 attached to rib bones 15 or transverse processes 16. The attachment members 110 can include a clamp 120-screw 114 combination (shown in FIGS. 3(*a*)-3(*e*)), or other suitable combination to secure the attachment members 110 to the transverse process 16 or rib bone 15.

Figure 4A:
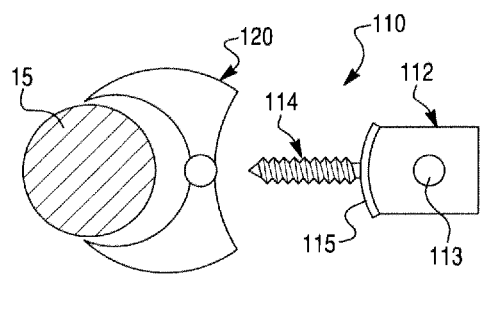
FIGS. 4(a) and 4(b) illustrate an attachment member according to another embodiment.
Figure 4B:
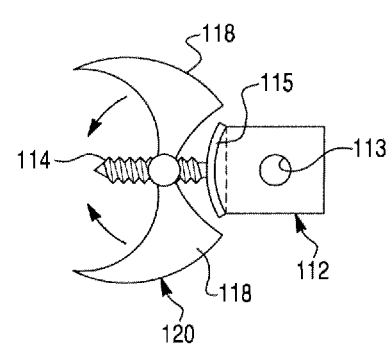

The clamp 120 can, for example, fit at least around a portion of a rib bone 15 or transverse process 16 or lamina 19 or caudal articular process or facet joint. The clamp 120 can include an upper arm 126 with a shoulder portion 126*a*, a lower arm 128 with a shoulder portion 128*a*, and a hinge 124 about which the arms 126, 128 pivot. The hinge 124 can include an opening 124*a* for the screw 114. As can be seen in FIG. 4(*b*), the screw 114 can be inserted through the opening 124*a*. Each arm 126, 128 can include shoulder portions 126*a*, 128*a* adjacent to a screw head 115 when the screw 114 is inserted through the clamp 120 and into the rib bone 15 or transverse process 16. The clamp 120 can include a lever arm portion 121, which is best shown in FIGS. 3(*a*), 3(*c*) and 3(*d*). As the upper 126 arm and lower arm 128 rotate about the hinge 124 toward each other into a clamped position (FIG. 3(*d*)), the lever aim portion 121 rotates. For example, in FIG. 3(*c*), the lever arm portion 121 is in a different position in an open (unclamped position) then when the clamp is in a clamped position about a rib bone 15, such as shown in FIG. 3(*d*).

The clamp 120 can move into a clamped position (FIG. 3(*d*)) by action of the screw 114. As the screw 114 is advanced through the clamp 120 and, thus, hinge 124 and hinge opening 124*a*, threads in the hinge opening 124(*a*) (not shown) correspond to and fit the screws on the screw 114. When the screw 114 is tightened into placement in the rib bone 15, the screw head 115 pushes against shoulders 126*a*, 128*a* of the upper arm 126 and lower arm 128. The pushing movement against the shoulders 126*a*, 128*a* is configured to rotate the upper arm 126 and lower arm 128 toward each other and into a clamped position. The shoulders 126*a*, 128*a* are offset from the hinge 124, the motion of the screw head 115 against the shoulders 126*a*, 128*a* forces the arms 126, 128 to clamp into a closed position.

Figure 28:
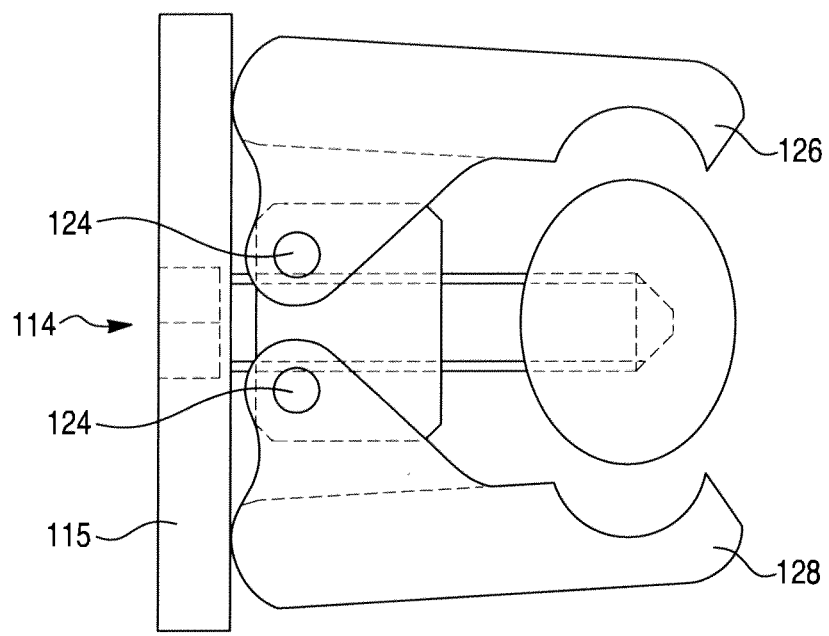
FIG. 28 illustrates a side view of an attachment member with multiple hinges.

Alternatively, the clamp 120 can have multiple hinges 124 (FIG. 28). In such a configuration, the upper arm 126 and the lower arm 128 each rotate about a separate hinge 124. By having multiple hinges, the relationship between the screw head 115 and clamp arms 126, 128, as the screw 114 is advanced, is different than if just a single hinge 124 (such as shown in FIG. 3(*a*)) is used to pivot both the upper and lower arms 126, 128. The additional hinge 124 would affect the rate at which the upper arm 126 and lower arm 128 approach one another as the screw 114 advances so that the screw head 115 pushes on the clamp arms 126, 128 to force the clamp arms 126, 128 to pivot about their respective hinges 124.

Referring to FIGS. 4(*a*) and 4(*b*), the clamp 120-screw 114 combination can include a wedge portion 118. The wedge portion 118 is connected to or integral with the clamp 120 and is adjacent to the clamp hinge 124. When the screw 114 is tightened, the screw 114 abuts the wedge portion 118, which levers the clamp 120 to tighten around the rib bone 15. As the screw head 15 is tightened, the screw head 15 pushes against the clamp 120 and wedge portion 118 to tighten the clamp 120 against the rib bone 15, thus moving the upper arm 126 and lower arm 128 toward each other into a clamped position.

Figure 7A:
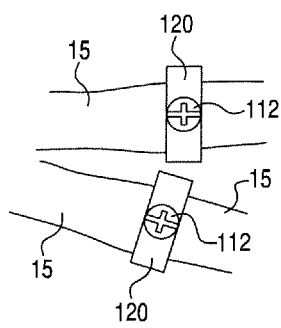
FIGS. 7(a)-7(c) illustrate attachment members and a spacer member according to an exemplary embodiment.

Each attachment member 110 also includes a connector or connector member 112, such as shown in FIGS. 4(*a*) and 4(*b*), for seating a spacer member 150, such as shown in FIGS. 7(*b*) and 7(*c*). The connector member 112 can be connected to or integral with the screw head 115. The connector member 112 geometry can vary depending upon the particular spacer member 150; preferably the connector member is in the shape of a plate. In FIGS. 4(*a*) and 4(*b*), the connector member 112 can include an opening 113 to engage with a corresponding spacer member 150. The spacer member 150 can have a suitable geometry, such as a projection, to mate with and attach (preferably releasably) with the opening 113.

Referring to FIG. 5(*a*), the clamp 120-screw 114 combination is shown in which the screw 114 includes a connector member 112 having protrusions 117 (or pegs) extending from opposite sides of the connector member 112. The protrusions 117 are provided to attach (preferably releasably) to a corresponding portion of a spacer member 150. For example, the protrusions 117 could extend into a corresponding hole in a spacer member 150.

Referring to FIG. 5(*b*), a clamp 120-screw 170 combination is shown attached to a rib bone 15 according to another embodiment. In this embodiment, the screw 170 includes a screw head 172 with a geometry configured to couple with and releasably engage with a corresponding spacer member 150. The screw head 172 can include a generally rectangular protrusion or extension 174 that protrudes out from a top surface 173 of the screw head 172. For example, the protrusion 174 could extend into a corresponding hole in a spacer member 150. In an exemplary embodiment, the attachment member 110, such as the clamp 120-screw 170 combination of FIG. 5(*b*), does not extend all the way around a rib bone 15. For example, the clamp 120 may attach only to opposite sides of the rib bone 15, but it need not encircle the rib bone 15. The clamp 120-screw 170 combination also is rotationally stable because the screw 170 prevents the clamp 120 from rotating around or sliding along the rib bone 15 despite the clamp 120 being non-circumferential. The screw 170 extends through a portion of the clamp 120 and tightens (screws) into the rib bone 15 or transverse process 16. The screw 170 can act as a barrier to rotational or sliding movement of the clamp 120 when screwed into the rib bone 15 or transverse process 16.

Referring to FIG. 5(*c*), a clamp 120-screw 180 combination is shown attached to a rib bone 15 according to another embodiment. In this embodiment, the screw 180 can include a screw head 182 with a rounded protrusion 184 extending from the screw head 182. The rounded protrusion 184 includes a hole or passage 185 for receiving an alignment member or rod 220 (see FIG. 6) or any other suitable connector component of a corresponding spacer member 150. As the rib bones 15 are realigned and move, the rod 220 is capable of sliding within the opening 220. The rod 220 may be rigid, flexible, or expandable and can span multiple spinal levels. The rod 220 may be coupled to (via another protrusion 184 and hole 185, or other suitable connection) to another attachment member 110 attached to a different rib bone 15 or transverse process 16.

Referring to FIG. 5(*d*), a clamp 120-screw 190 combination is shown attached to a rib bone 15 according to another embodiment. In this embodiment, the screw 190 can include a screw head 192 with a geometry configured to couple with and releasably engage with a corresponding spacer member 150. The screw head 192 can include a generally rounded protrusion or extension 194 that protrudes out from a top surface 193 of the screw head 192. The protrusion 194 can include a well 195 or opening that does not pass completely through the protrusion. The well 195 and protrusion 194 are configured to couple with a corresponding spacer member 150. For example, the well 195 could engage with a corresponding projection on the spacer member 150.

Figure 5A:
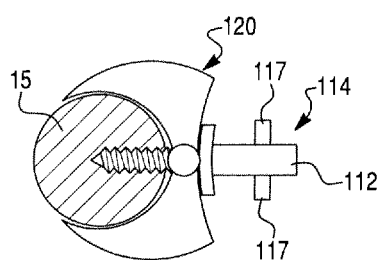
FIG. 5(a) illustrates a side view of an attachment member attached to a rib in which a plate includes a protrusion according to an exemplary embodiment.
Figure 5B:
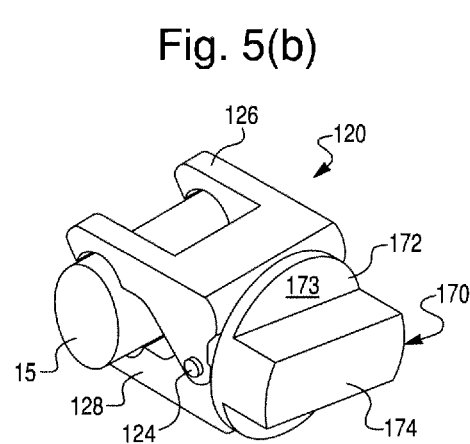
FIG. 5(b) is a perspective view of an attachment member according to another embodiment.
Figure 5C:
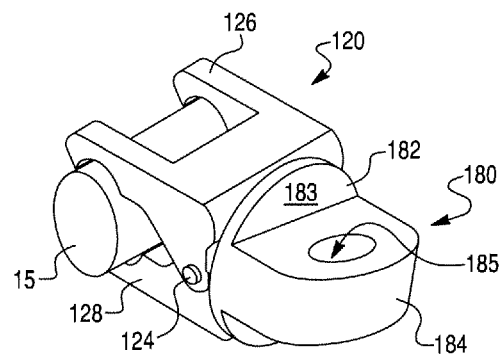
FIG. 5(c) is a perspective view of an attachment member according to another embodiment.
Figure 5D:
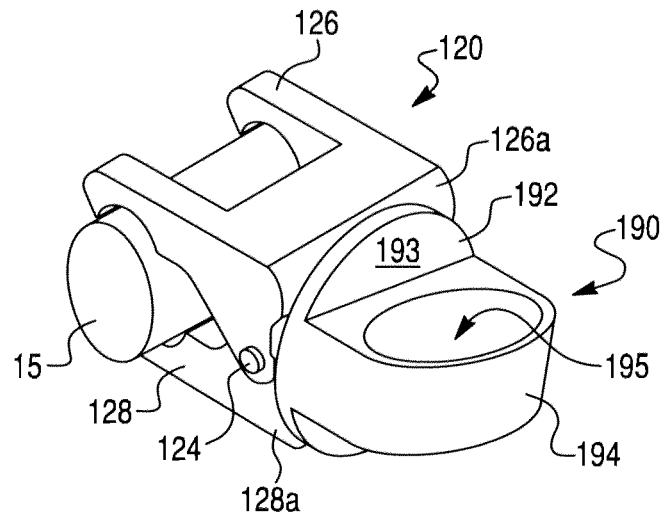
FIG. 5(d) is a perspective view of an attachment member according to another embodiment.
Figure 5E:
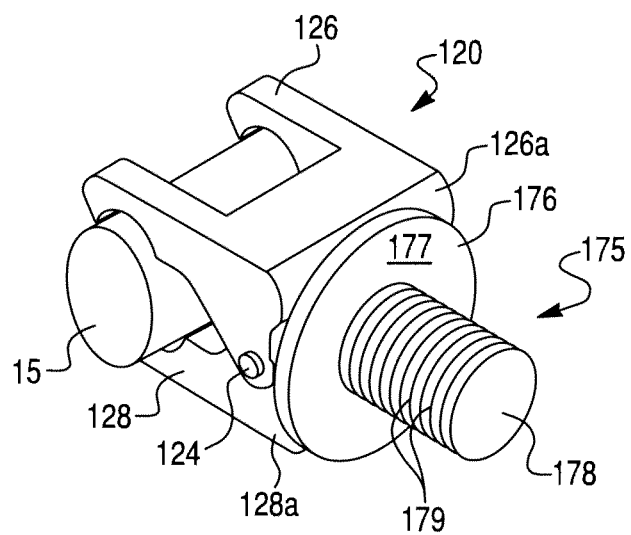
FIG. 5(e) is a perspective view of an attachment member according to another embodiment.

Referring to FIG. 5(e), a clamp 120-screw 175 combination is shown attached to a rib bone 15 according to another embodiment. In this embodiment, the screw 175 can include a screw head 176 with a geometry configured to couple with and releasably engage with a corresponding spacer member 150. The screw head 176 can include a threaded protrusion or peg 178 that protrudes out from a top surface 177 of the screw head 176. The protrusion 178 includes threads 179 that are configured to mate with corresponding threads on a spacer member 150.

Figure 6:
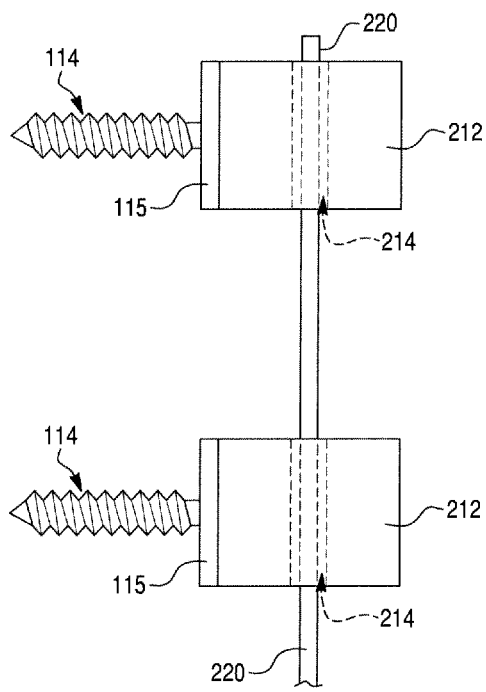
FIG. 6 illustrates a side view of first and second screws that each include plates according to another exemplary embodiment, in which a rod extends through the plates of the first and second screws.

Referring to FIG. 6, a screw 114 and connector member 212 are shown. The connector member 212 includes an opening (passage or channel) 214 for an alignment member or rod 220 to slide through. As the rib bones 15 are realigned and move, the rod 220 is capable of sliding within the opening 214. The rod 220 may be rigid, flexible, or expandable and can span multiple spinal levels. The rod 220 may be coupled to (via another connector member 212, or other suitable connection) to another attachment member 110 attached to a different rib bone 15 or transverse process 16. For example, FIG. 6 illustrates the rod 220 extending through two adjacent screws 114 and corresponding connector members 212. The rod 220 is configured to connect all attachment members 110 and can be used to align attachment points on rib bones 15. For example, the openings 220 on the connector members 212 of all attachment members 110 must all be sufficiently aligned such that the rod 220 can slide through all of the openings 220. The rod 220 can also help improve spinal growth by helping direct movement of the rib bones 15 by aligning the rib bones 15. The rod 220 is preferably unthreaded and is slidably positioned within all of the openings 220.

According to an exemplary embodiment, spacer members 150 may be positioned between attachment members 110 and result in the lengthening of the assembled orthopaedic device 100. The spacer members 150 may allow motion (bending or twisting or flexing) between the attachment members 110. The motion may be constrained so as to only allow bending in a single direction by selection of appropriate materials for the spacer member 150. For example, the spacer member 150 can comprise a polymer as described below.

Figure 7B:
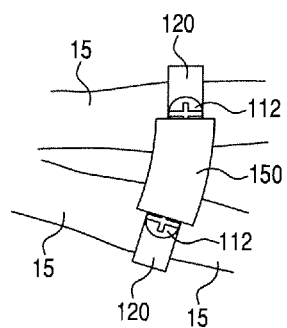
Figure 7C:
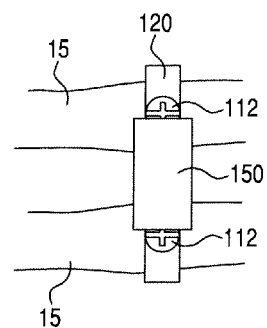

Spacer members 150 are inserted at the time of surgery in a compressed form between adjacent attachment members 110. Once the entire orthopaedic construct is assembled, the spacer members 150 are allowed to expand, which gives correction to the deformity (see FIGS. 7(b) and 7(c)). FIGS. 7(b) and 7(c) generally show a spacer member 150 for explanatory purposes. The spacer members 150 not only expand longitudinally, but also may have some bending ability so as not to overly constrain the assembly and, thus, allow a small degree of spinal mobility. According to an exemplary embodiment, the orthopaedic device 100 initially is positioned in a bent form, such as shown in FIG. 7(b). When the spacer member 150 expands, the spacer member 150 straightens, such as shown in FIG. 7(c). The spacer member 150 can produce a corrective force of, for example, 50 to 200 N.

The spacer members 150 may be positioned posterior to or lateral to the attachment members 110. The spacer members 150 may also be anterior to the attachment members 110, such as when the device 100 is placed from an anterior approach to the rib heads 14 via the chest. Referring to FIG. 1(b), which illustrates the spine 10 from an anterior view, the attachment members 110 and spacer members 150 can be attached to the rib bones 15 from a frontal (anterior) approach that reverses the direction which the attachment members 110 and spacer members 150 face. In other words, if the screw head 115 faces towards a back-side of a patient with the orthopaedic device, the screw head 115 in the anterior position would face the front-side of the patent.

Figure 8:
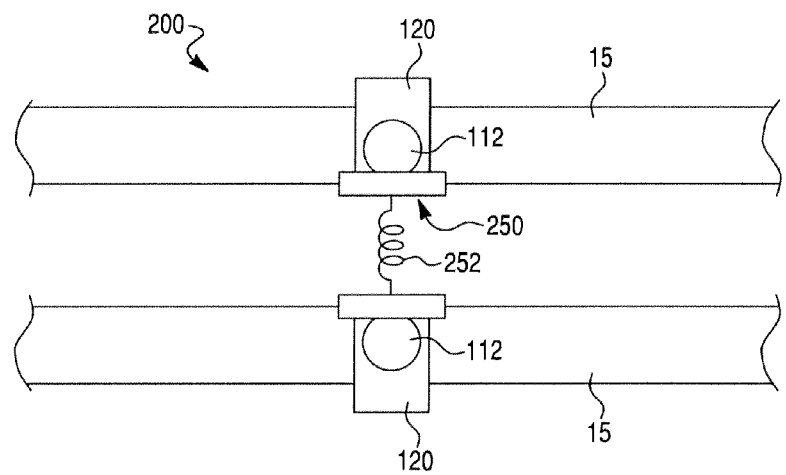
FIG. 8 illustrates an orthopaedic device attached to adjacent ribs with a spacer member comprising a spring attached to the attachment members according to an exemplary embodiment.

One possible type of spacer member 250 is a spring 252, such as shown in FIG. 8. The spring 252 may be a nitinol spring that is implanted between the attachment members 110 in a compressed state and then simultaneously expanded with those at other spinal segments. The spring 252 may be fabricated of nitinol or another suitable metal that can be induced to change shape or expand. The spring 352 may comprise a shape memory alloy. The spring 252 may be a coil spring.

Figure 9A:
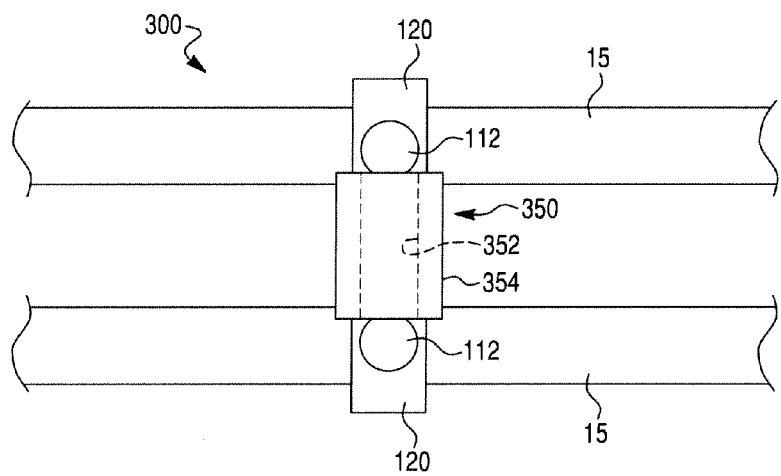
FIGS. 9(a) and 9(b) illustrate a spacer member according to another embodiment.
Figure 9B:
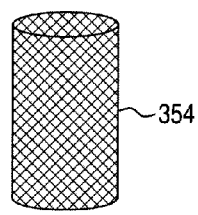

Referring to FIGS. 9(a) and 9(b), the spacer member 350 may be a polymer 352 in an alternative embodiment. The polymer 352 may be a hydrogel that can be induced to change shape or expand. For example, the polymer 352 may comprise a polyvinyl hydrogel. The spacer member 350 may be fabricated by certain polymeric hydrogels, which may be inserted in a dehydrated state and then expand as they absorb water from the surrounding muscle tissues that overlie the assembly after completion of the surgery. The polymer 352 may also include a housing 354. The housing 354 can be a fabric housing. The fabric housing 354 can comprise a wire mesh, such as shown in FIG. 9(b).

The spacer member 350, according to an exemplary embodiment, may have a composite with a reinforcing fiber pattern within the polymer matrix 352 to allow expansion in a preferential (e.g., longitudinal) direction.

Another type of spacer member 150 may be electromagnetic with a small motor (not shown). The electromagnetic motor may have a housing that expands in the presence of an applied magnetic field. The electromagnetic motor may incorporate a screw that elongates in the presence of an applied magnetic field which thus produces an elongation and distractive force between the attachment members 110.

In alternative embodiments, the spacer member 150 may include a threaded turnbuckle assembly, such as shown in FIGS. 10(a) and 10(b). The screw 114 includes a connector portion 412 with a passage or opening 414. The interior of the passage 414 is threaded to mate with threads on a threaded rod or member 420. The rod can extend between two or more attachment members 110 and is threadably attached to the connector portion 412. A nut 422 can be positioned on the threaded rod 420 adjacent to connector portion 412. The threaded rod 420 and connector portion 412 (turnbuckle assembly) can be adjusted to provide a distraction force by movement of the threaded rod 420 within the passages 414 of adjacent connector portions 412. The threaded rod 420 can be threaded into the passages 414 to have the connector portions 412 (and thus, attachment members 110 and attached rib bones 15) closer together, such as shown in FIG. 10(a). Unthreading the threaded rod 420 from the passages 414 can push the connector plates 412 apart to provide a distraction force on the associated rib bones 15.

Figure 12:
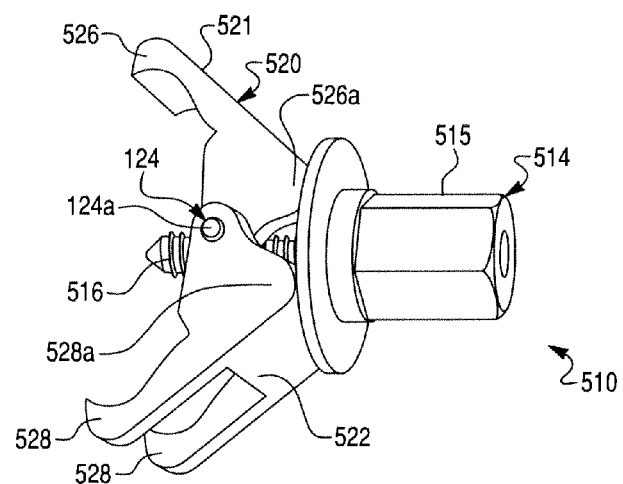
FIG. 12 illustrates a perspective view of an attachment member with a clamp/screw combination.
Figure 13:
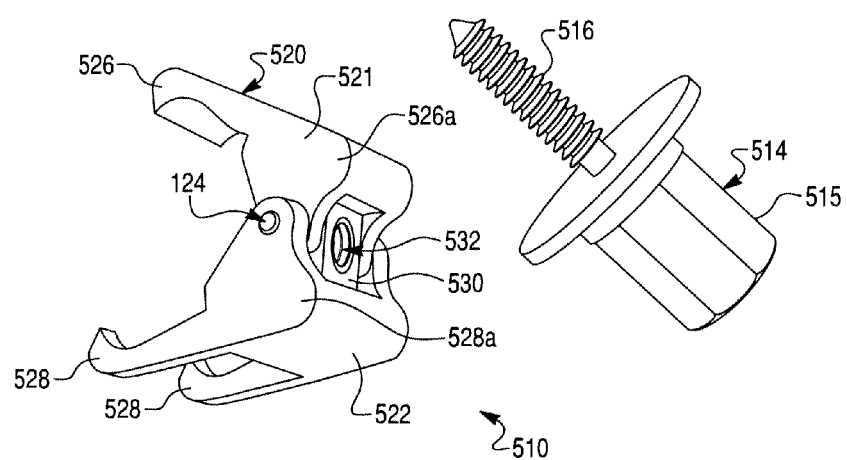
FIG. 13 illustrates an exploded view of the attachment member with the clamp/screw combination of FIG. 12.

Referring to FIGS. 12 and 13, an attachment member 510 of an orthopaedic device 100 is shown which includes a clamp 520-screw 514 combination with a block 530 component. The clamp 520 includes an upper body 521 and a lower body 522. The upper body 521 includes a shoulder 526a and upper arm 526. The lower body 522 includes a shoulder 528a and lower arms 528. The clamp 520 further includes a hinge 124 about which the upper body 521 and lower body 522 pivot.

The block 530 is positioned between the upper body 521 and the lower body 522 and is connected to the hinge 124. The block 530 is connected to the hinge 124 via a hinge pin, screw, or other projection or fastener. The block 530, as shown in FIGS. 12 and 13, is a separate, but connected, component of the attachment member 510. The hinge (pin) 124 can be screwed, press-fit or welded onto the block 530 to fix the hinge 124 into the block 530. Alternatively, the hinge 124 could be offset from the block 530. The block 530 could also be a unitary and integral part of the clamp 520, such as in the attachment member of FIG. 18 (block not shown).

The block 530 includes an opening 532 to receive the screw 514. The screw 514 includes a screw head 515 and threads 516. The screw 514 is inserted into the block 530 and, thus, clamp 520 via the opening 532. The opening 532 may include internal threads (not shown) to mate with the threads 516 on the screw 514.

Figure 16:
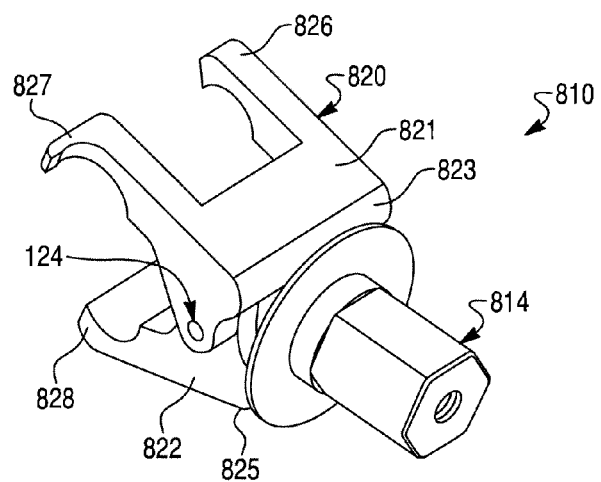
FIG. 16 illustrates a perspective view of an attachment member with a clamp/screw combination with upper arms that diverge asymmetrically.
Figure 17:
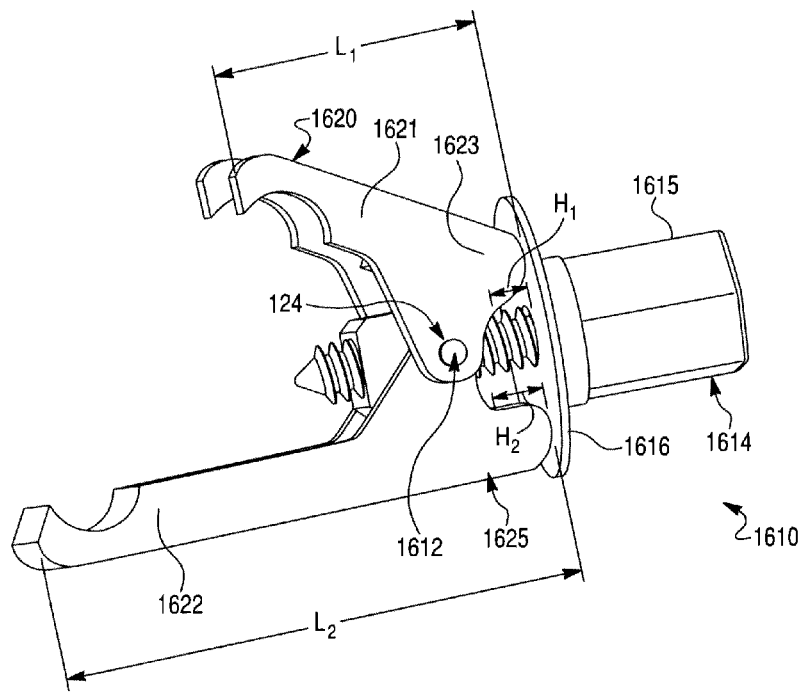
FIG. 17 illustrates an attachment member with a clamp/screw combination in which shoulders on the arms are asymmetrical and the length of the arms are different.
Figure 18:
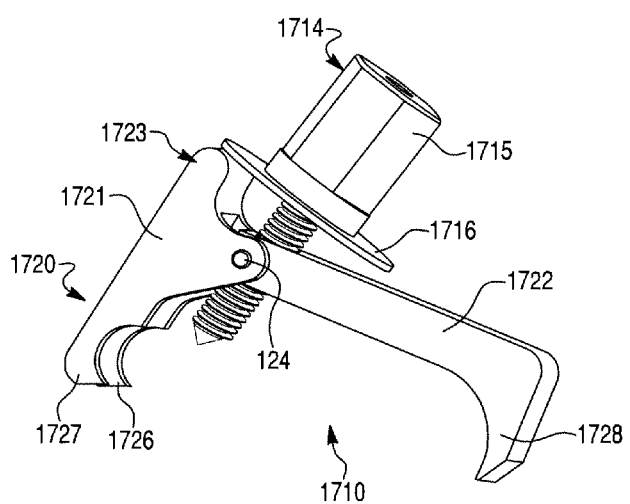
FIG. 18 illustrates an attachment member with a clamp/screw combination in which upper arms are mobile and a lower arm is fixed.

Referring to FIGS. 16-18, attachment members 810, 1610, 1710 can include at least one clamp arm that is asymmetrical relative to other clamp arms and/or a clamp body that is asymmetrical to the other clamp body.

For example, FIG. 16 illustrates the attachment member 810 that includes a screw 814 inserted into a clamp 820 with asymmetric clamp arms 826, 827, 828. The clamp 820 includes an upper clamp body 821 with a shoulder 823 and first and second upper arms 826, 827. The clamp 820 includes a lower clamp body 822 with a shoulder 825 and a single lower clamp arm 828. The upper clamp body 821 is asymmetrical from the lower clamp body 822 at least because the upper clamp body 821 includes two arms 826, 827, whereas the lower clamp body 822 includes a single arm 828.

In addition, the first upper arm 826 is asymmetrical from the second upper arm 827. The asymmetry of the upper arms 826, 827 assists in attachment to the rib bone 15 or other spinal elements. For example, the clamp 820 can be used to grab or clamp onto the thoracic spin by having the downward facing arm (first upper arm) 826 grab or hook the lateral lamina while have the side facing arm (second upper arm) 827 grab or hook the medial aspect of the transverse process.

FIG. 17 illustrates the attachment member 1610 that includes a screw 1614 and a clamp 1620 with asymmetric shoulders 1623, 1625. The screw 1614 includes a screw head 1615 and flange 1616. The clamp 1620 includes an upper body 1621 with an upper shoulder 1623 and a lower body 1622 with a lower shoulder 1625. The upper body 1621 is asymmetrical from the lower body 1622 at least because the upper body 1621 has a length $L_1$ that is less than a length $L_2$ of the lower body 1622. The ratio of $L_2$ to $L_1$ can vary. For example, the ratio of $L_2$ to $L_1$ may be 2:1 or 3:2 for possible application to the lamina of the spine.

The upper shoulder 1623 of clamp 1620 is also asymmetrical relative to the lower shoulder 1625. The upper shoulder 1623 has a height $H_1$ that is less than a height $H_2$ of the lower shoulder 1625. The height H of a shoulder is determined by the distance from the hinge-to-shoulder interface to the flange 1616 of the screw 1614 (or top end of shoulder). In such a configuration, the upper body 1623 and lower body 1625 do not close together (move towards each other) in a symmetrical manner as the screw 1614 is advanced through the clamp 1620. Rather, because the lower shoulder 1625 is larger in height than the upper shoulder 1623, the lower clamp body 1622 will pivot into a closed or fully clamped position before the upper clamp body 1621 will move into a closed or fully clamped position. FIG. 17 illustrates the lower clamp body 1622 being fully closed or clamped whereas the upper clamp body 1621 is only partially closed or clamped. The ratio of $H_1$ to $H_2$ can vary. For example the ratio of $H_1$ to $H_2$ may range from 1.1:1 to 1.4:1.

FIG. 18 illustrates an attachment member 1710 that includes a screw 1714 and clamp 1720 in which a lower clamp arm 1728 is non-rotatable about the hinge 124. The screw 1714 includes a screw head 1715 and flange 1716. The clamp 1720 includes an upper body 1721 and a lower body 1722. The block 530 (not shown), the opening 532 (not shown) and the lower body 1722 faint a unitary piece. The upper body 1721 includes a shoulder 1723 and two clamp arms 1726, 1727. The lower body 1722 includes the lower clamp arm 1728. The lower clamp arm 1728 and lower body 1722 are fixed so that the lower body 1722 and lower clamp arm 1728 do not pivot about the hinge 124. The upper clamp arms 1726, 1726 (and, thus, upper body 1721) pivot about the hinge 124 when the screw 1714 is advanced through the clamp 1720. In this configuration, the flange 1716 of the screw 1714 is non-perpendicular to the lower clamp arm 1728 when the screw 1714 is inserted into the clamp 1720.

Referring to FIGS. 14-15 and 26-27, an attachment member of the orthopaedic device 100 can include a projection for receiving a spacer member 151 to connect the attachment member to a second attachment member in a generally vertical direction. The spacer member 151 can fix repositioned vertebral bodies into position by fixing an upper attachment member and a lower attachment member together. For example, FIG. 2 illustrates an upper attachment member 610 and a lower attachment member 610 connected by a spacer member 151.

Figure 14:
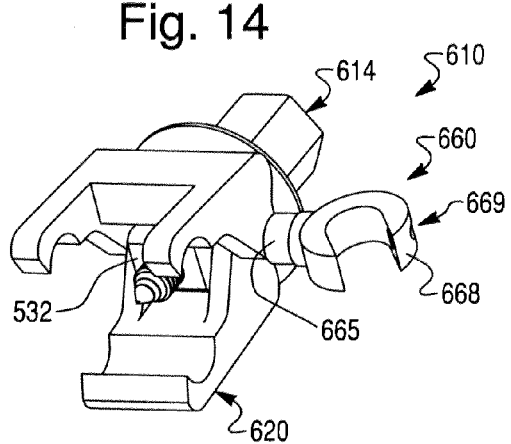
FIG. 14 illustrates a perspective view of an attachment member with a clamp/screw combination that includes a projection extending from a hinge.

For example, FIG. 14 illustrates an attachment member 610 with a projection 660 extending from the hinge 124. The attachment member 610 includes a screw 614 and a clamp 620. The clamp 620 includes the projection 660 extending from the hinge at a hinge projection body 665. The projection 660 includes a U-shaped portion 668 with a slot to allow the spacer member 151 to slide within the U-shaped portion 668 to assist with alignment of the orthopaedic device 100. The spacer member 151 can also be rigidly fixed within the U-shaped member 668 to connect the attachment member 610 to a second attachment member 610. The second attachment member 610 would be positioned either above or below the first attachment member 610 (FIG. 2). The U-shaped portion 668 includes a screw opening 669 for insertion of a set screw (not shown). The set screw can be advanced through the screw opening 669 to fix the 151 in the U-shaped portion 668.

Figure 15:
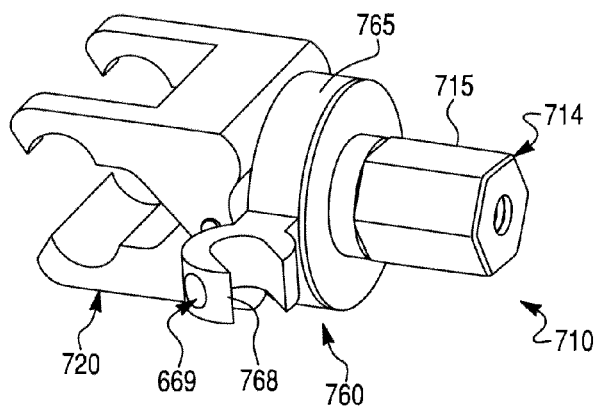
FIG. 15 illustrates a perspective view of an attachment member with a clamp/screw combination that includes a projection coupled to the screw.

FIG. 15 illustrates an attachment member 710 with a projection 760 for receiving a spacer member 151 to connect the attachment member to a second attachment member in a vertical direction. The attachment member 710 includes a clamp 720 and screw 714 with a screw head 715. The projection 760 extends from a projection body 765 that is clamped or positioned between shoulders of the clamp 720 and the screw head 715 to couple the projection 760 to the attachment member 710. The projection body 765 may be washer (circular disc shaped with a central opening) or C-shaped to clamp or affix around the screw head 715.

The projection 760 includes a U-shaped portion 768 with a slot to receive the spacer member 151. Similar to the projection 660, the spacer member 151 can be slidable within or fixed to the U-shaped portion 768. The spacer member 151 can be fixed to the U-shaped portion 768 by a set screw (not shown) that is positioned in a set screw opening 669 in the U-shaped body 768.

Figure 26:
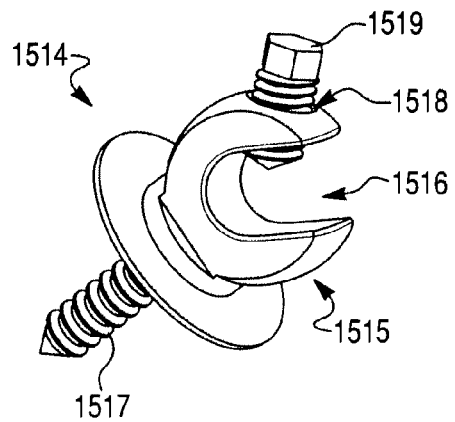
FIG. 26 illustrates a perspective view of a screw for an attachment member, the screw including a screw head projection with a U-shape.
Figure 27:
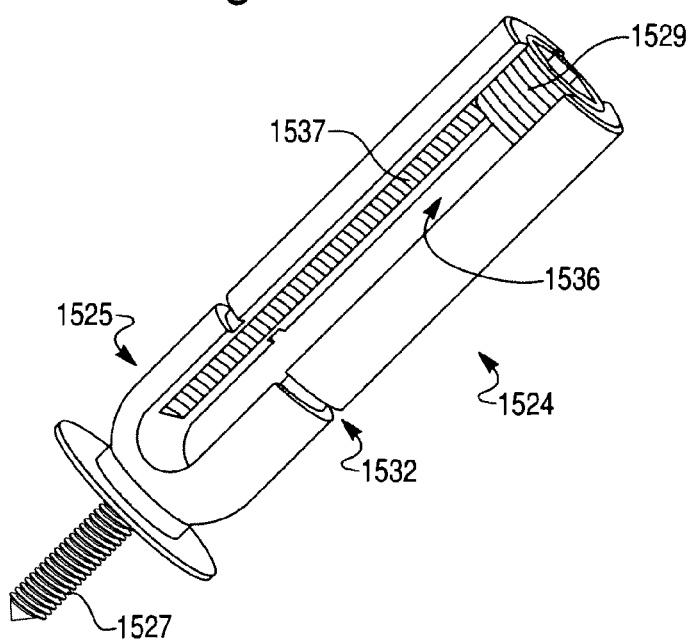
FIG. 27 illustrates a perspective view of a screw for an attachment member, the screw including a screw head projection with a cylindrical shape and internal threads.

FIGS. 26 and 27 illustrate a screw head including the projection for receiving the spacer member 151 to connect an attachment member to a second attachment member. Referring to FIG. 26, the screw 1514 can include a screw head 1515 and threads 1517. The screw head 1515 is a projection in the form of a U-shaped body with a slot 1516. The spacer member 151 can slide within the slot 1516 to assist with alignment of the orthopaedic device 100 or the spacer member 151 can be rigidly fixed within the slot 1516. The slot 1516 includes a screw opening 1518 for insertion of a set screw 1519. The set screw 1519 can be advanced through the screw opening 1518 to fix the spacer member 151 in the slot 1516.

Referring to FIG. 27, the screw 1524 can include threads 1527 and a screw head 1525. The screw head 1525 is a projection in the form of a cylindrical body with a slot 1536. The screw head 1525 may comprise semi-cylindrical parts with the slot 1536. The slot 1536 includes internal threads 1537 for a set screw 1529.

The spacer member 151 can slide within or be rigidly fixed within the slot 1536. Once the spacer member 151 is positioned within the slot 1536, the set screw 1529 is advanced down through the internal threads 1537 into a reduced or fixed positioned. Excess screw head 1525 (i.e., portions of screw head 1525 above the set screw 1529) may be broken off at a notch 1532. The notch 1532 is a notched circumferential weakened region that permits a surgeon to manually break off the excess screw head 1525. In the configuration shown in FIG. 27, two notches 1532 are shown. However, the screw head 1525 can have any suitable number of notches 1532.

Alternatively, the projection for receiving a spacer member 151 to connect two attachment members together may be connected to any suitable component of each attachment member (e.g., clamp arm, shoulder, hinge, or screw head).

Referring to FIGS. 19-22, the orthopaedic device 100 can include two side-by-side attachment members that are fixedly or relcasably connected by a strut. The strut allows a generally horizontal connection (i.e. substantially perpendicular to the spine) between attachment members that are arranged between vertebra or within a vertebral segment so that a surgeon may lever and axially rotate the vertebra. For example, FIG. 2 illustrates two side-by-side attachment members 910, 910 that are connected by a strut 950. The strut 950 can be of any suitable size and length to allow for variations in anatomy and distance between spinal fixation locations such as the right and left laminae. Alternatively, the strut could allow a connection in an orientation other than horizontal. For example the strut could allow a generally vertical connection (i.e. substantially parallel to the spine).

Figure 19:
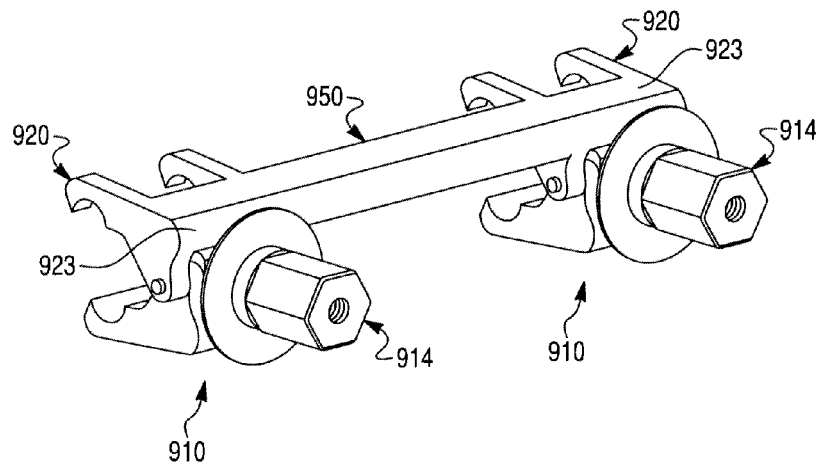
FIG. 19 illustrates a perspective view of two attachment members with clamp/screw combination that are connected by a strut.

FIG. 19 illustrates two attachment members 910 that are connected by a strut 950. Each attachment member 910 includes a clamp 920 and screw 914. Each clamp 920 includes an upper shoulder 923. The strut 950 is a continuous extension of the upper shoulder 923 of each of the clamps 920 so that the strut 950 is a unitary and integral part of both of the attachment members 910. The connection of the strut 950 to the attachment members 910 forms a single device. As an example, the attachment members 910 can be fixed to lamina of the spine. By having an additional fixation double attachment member in one device, the arrangement gives for example, a surgeon, an ability to apply axial moments to the spine.

Figure 20:
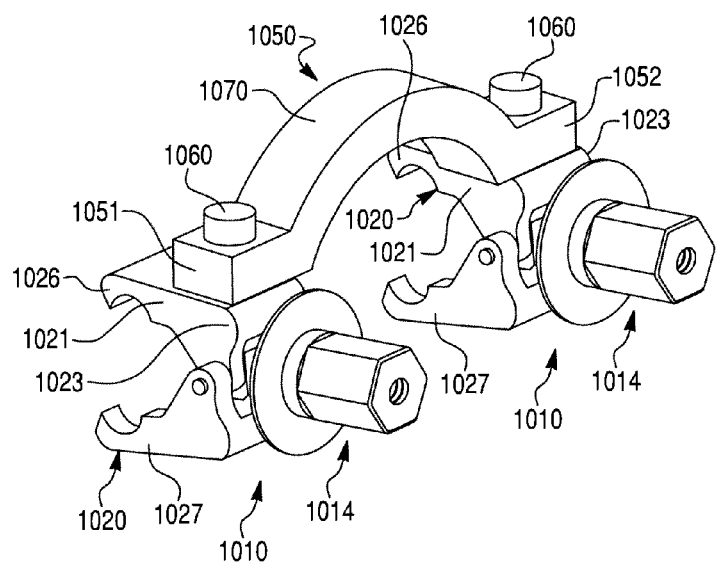
FIG. 20 illustrates a perspective view of two attachment members with clamp/screw combination that are connected by a strut releasably connected to each clamp.

FIG. 20 illustrates two attachment members 1010 that are connected by a strut 1050. Each attachment member 1010 includes a clamp 1020 and a screw 1014. Each clamp 1020 includes a lower arm 1027 and an upper clamp body 1021 with an upper arm 1026 and a shoulder 1023.

The strut 1050 includes a first connecting end portion 1051, a second connecting end portion 1052 and an arched portion 1070 between the connecting end portions 1051, 1052. The arched portion 1070 can have a curve or arch of a suitable shape and size to account for specific anatomy (e.g., spinous process) or to permit a surgeon to place bone graft below the arched portion 1070 during a spinal fusion procedure. As an example, the upper clamp arms 1026 can grab or hook the lamina medially and the transverse process laterally, while the lower clamp arms 1027 can grab or hook the facet joint. Such an arrangement would give a surgeon an ability to apply axial moments to the spine.

The strut 1050 is fixedly or releasably connected to one or more of the clamps 1020 by fasteners 1060. The fasteners 1060 fix the strut 1050 to each clamp 1020 at the upper clamp body 1021. The fasteners 1060 can be screws, bolts, nuts, or any other suitable fastener.

Figure 21:
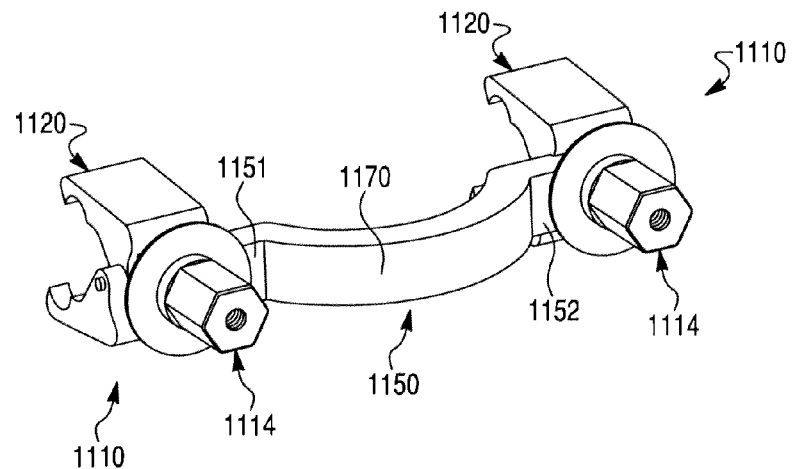
FIG. 21 illustrates a perspective view of two attachment members with clamp/screw combination that are connected by a strut releasably connected by each screw.

FIG. 21 illustrates two attachment members 1110 connected by a strut 1150. Each attachment member 1110 includes a clamp 1120 and a screw 1114. The strut 1150 includes first and second connecting end portions 1151, 1152 with an arched portion 1170 therebetween. The strut 1150 is connected to each of the attachment members 1110 by being fixed by each screw 1114 when the screw 1114 is fixed into the corresponding clamp 1120. The first and second connecting end portions 1151, 1152 include openings (not shown) to permit the screws 1114 to pass through and connect the strut 1150 to each screw 1114-clamp 1120 combination.

Figure 22:
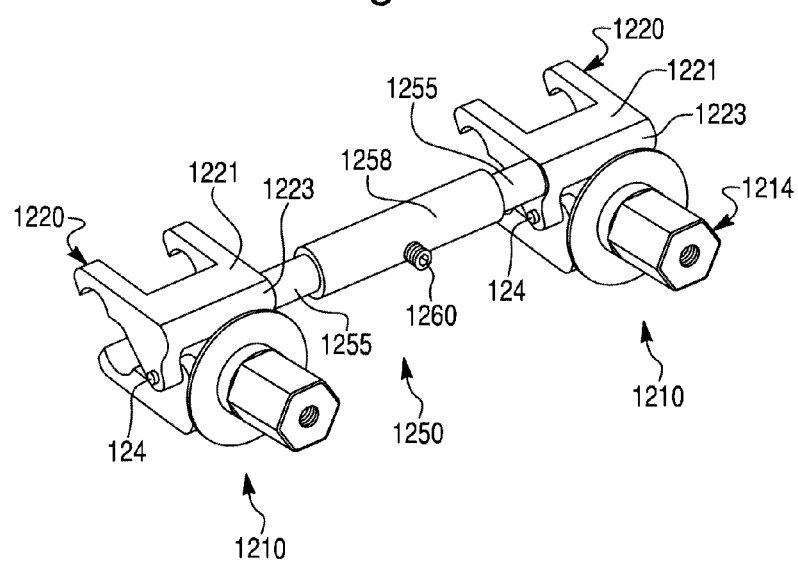
FIG. 22 illustrates a perspective view of two attachment members with clamp/screw combination that are connected by a telescoping strut.

FIG. 22 illustrates two attachment members 1210 connected by a telescoping strut 1250. Each attachment member 1210 includes a screw 1214 and a clamp 1220. The clamp 1220 includes an upper body 1221 with a shoulder 1223. The strut 1250 includes a strut body 1255, telescoping housing 1258 and a set screw 1260. The strut body 1255 extends from the upper body 1221 at or near the shoulder 1223. The strut body 1255 can be integral and unitary with the upper body 1221 or be separate, but connected components. The strut body 1255 can be adjusted relative to the telescoping housing 1258 to adjust the length of the strut 1250. The set screw 1260 can then be fixed into the strut 1260 to set or fix the strut 1250 at a desired length. In addition, the strut body 1255 extending from one attachment member 1210 could also be rotated relative to the strut body 1255 extending from the other attachment member 1210.

Referring to FIGS. 19-22, the struts 950, 1050, 1150, 1250 can be rigid or semi-rigid. The struts 950, 1050, 1150, 1250 can be semi-rigid by, for example, being comprised of a material sufficiently pliable to permit manual bending or contouring of the strut 950, 1050, 1150, 1250.

Figure 23:
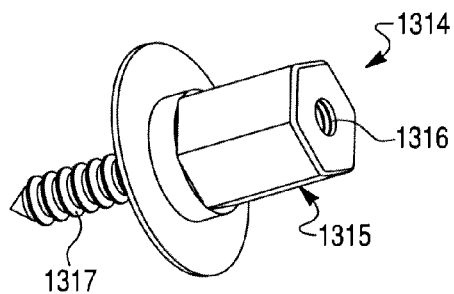
FIG. 23 illustrates a perspective view of a screw for an attachment member, the screw including a course thread.
Figure 24:
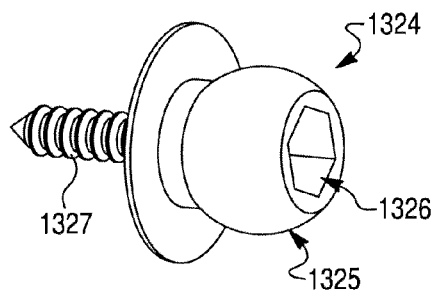
FIG. 24 illustrates a perspective view of a screw for an attachment member, the screw including a spherical shape with a recess.
Figure 25:
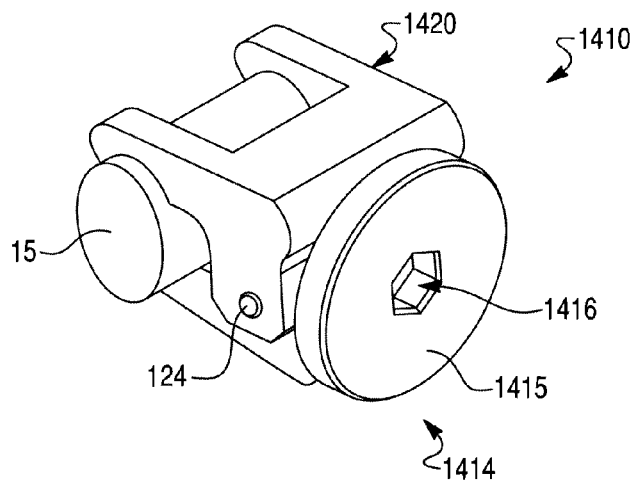
FIG. 25 illustrates an attachment member with a clamp/screw combination in which the screw includes a flat screw head with a recess.

Referring to FIGS. 23-25, screws 1314, 1324, 1414 with varying configurations are shown. Attachment members of the orthopaedic device 100 can have one or more configurations of screws, such as those shown in FIGS. 23-25. The shape of the screw or screw head can allow for fixation of other devices. For example, as shown in FIG. 23, a screw 1314 can include a screw head 1315 and threads 1317. The screw head 1315 is hexahedron shape with a recess 1316. The recess 1316 is provided in the screw head 1315 to allow a screwdriver to turn the screw 1314.

The recess 1316 can extend through an entire length of the screw 1314 to form a cannula (or interior tube or passageway) for the screw 1314. The cannulated recess 1316 is configured to allow for a tool or other instrument to be inserted through the screw 1314 to guide the screw 1314 as it is advanced into the clamp, to hold the screw 1314 and/or orthopaedic device 100 against the bone provisionally during surgery, or to access an internal region of the rib bone 15, transverse process 16, lamina 19 or other structure to which the screw 1314 is fixed into.

The threads 1317 can be a fine or course thread. For example, the threads for a cortical bone can be finer than for a cancellous bone. The threads 1317 may be arranged on the screw 1314 so that the threads 1317 have a different degree of fixation to cortical bone relative to cancellous bone or other materials. In other words, a screw 1314 with threads 1317 may be chosen with a specific configuration that best works with cortical bone when being affixed to cortical bone as opposed to when the screw 1314 will be affixed to cancellous bone.

Referring to FIG. 24, the screw 1324 can have threads 1327 and a screw head 1325. The screw head 1325 is spherical in shape and includes a recess 1326, such as for insertion of a screw driver or other tool.

Referring to FIG. 25, an attachment member 1410 is shown that includes a clamp 1420 and a screw 1414. The screw 1414 is shown inserted into the clamp 1420 so that the clamp 1420 is closed or clamped around a rib bone 15. The screw 1414 has a screw head 1415 with a flat shape. The screw head 1415 further includes a recess 1416 for insertion of a screw driver or other tool.

The orthopaedic device can have multiple components, each including attachment members to attach to bone and a strut and/or a spacer member that allow segmental realignment of bone. The orthopaedic device 100 can be attached to the spine with the following steps (particular order may vary). A first attachment member 610 (see FIG. 2) is fixed to at least one of a rib bone, transverse process, lamina, articular process of a facet joint. A surgeon determines the position of the first attachment member over at least one of a rib bone, transverse process, lamina, articular process of a facet joint to which it will be affixed. A pilot hole (not shown) for the screw is made. The pilot hole can be formed by removing the screw from the clamp and inserting the drill through the opening 532 in the clamp to provide a more precise location of the pilot hole. The screw is then repositioned in the opening of the clamp and advanced through the clamp into the bone. Minor adjustments to the location of the screw may be made during advancement of the screw.

As the screw advances into the bone and through the clamp, the screw head engages the shoulders of the clamp. The pushing of the screw head on the shoulders of the clamp pivots the upper and lower arms of the clamp to a closed or clamped position about the bone, resulting in secure bony fixation at multiple points of the clamp and screw.

A second attachment member 910 (see FIG. 2) is fixed generally horizontal to and side-by-side with the first attachment member 610 to at least one of a rib bone, transverse process, lamina, articular process of a facet joint that is the same as or different from that which the first attachment member 610 is attached. A strut 950 is positioned to connect the first 610 and second 910 attachment members together in a generally horizontal manner.

A surgeon can grasp the strut 950 with a handle or joystick to manipulate or reposition vertebral bodies as desired. Once the vertebral bodies are suitably repositioned, the first or second attachment member 610 can be fixed to a third attachment member 610 (see FIG. 2) in a generally vertical direction (i.e. substantially parallel to the spine) by a spacer member 151. The spacer member 151 is connected to the attachment members 610, 610 by the projections. The connecting of the spacer member 151 in the generally vertical direction fixes or maintains the position of the repositioned vertebrae. After fixing of the spacer member 151, the strut 950 can be removed. Alternatively, the strut 950 can remain in place. Alternatively, the first or second attachment members could be fixed to a third attachment member in an orientation other than vertical. For example the first or second attachment members could be fixed to a third attachment member in a generally horizontal direction (i.e. substantially perpendicular to the spine).

The strut 950 allows a horizontal connection between attachment members 610, 910 that are arranged between vertebra or within a vertebral segment so that a surgeon may lever and axially rotate the vertebra. For example, in scoliosis, vertebrae may be rotated axially from the normal orientation. Fixation of side by side attachment members 610, 910 that are connected by a strut 950 provides secure fixation to the spine to allow for torsion correction of the rotated vertebra (derotation). The spacer member 151 can fix the rotated or moved vertebral bodies (such as after rotation by a surgeon with the strut) into position by fixing an upper attachment member 610 and a lower attachment member 610 (i.e., spacer member fixes two attachment members in a generally vertical direction). In addition to this rotational maneuver, the spacer member 150, 151 may be expandable and/or flexible, such as described in paragraph [0052], which allows a surgeon to obtain multi-dimensional correction of spinal malalignment.

The first 610, second 910 and third 610 attachment members may be similar members or different members and may be a combination of attachment members, clamps and screws discussed above.

Although the orthopaedic device 100 has been described as a fusionless device, according to another exemplary embodiment, the orthopaedic device 100 also may be used as a fusion device for internal fixation if combined with a bone-graft. For example, the device 100 can be used as a temporary splint or holding device to keep bones in a correct fused alignment/position until the bone graft is capable of fusing together the bones. When fusion of the bones is complete, the device 100 can be removed.

The FIGURES illustrate the clamp 120 attached to a rib bone 15, but it should be known that the clamp 120 could can also attach to a rib head 14, transverse process 16, lamina 19, or any other suitable location. According to an exemplary embodiment, the device 100 may be non-rigid and expandable.

The device 100 can also be made of a material that is biocompatible and/or include a biocompatible coating on the attachment members and/or spacer members to enhance fixation of the attachment members to bone comprised of a porous surface texture. The biocompatible coating/material can comprise, for example, hydroxyappetite. The device 100 can be made of different materials such that, for example, the material forming the screw is different than the material forming the clamp and/or the material forming the spacer member. As an example, the surface of the clamp may have a textured or porous bone ingrowth surface or surface coating treatment to enhance long-term fixation of the clamp/orthopaedic device to the vertebra. One example of a surface coating is hydroxyapatite.

The screw, clamp, and spacer member can be formed of material(s) with different electrical conductivities, such as if the device is used to splice into an electrical cable.

Attachment members 110 may or may not be placed at every spinal level. In particular cases, the implanting surgeon may desire to skip a spinal level. The attachment members 110 may be used at any spinal level. For example, such as shown in FIG. 11 a first attachment member 110 can be attached to a first rib bone 15 and a second attachment member 110 can be attached to a second rib bone 15 not adjacent to the first rib bone 15. The spacer member 150 can be positioned between the first and second attachment members 110 to provide distraction between the first and second rib bones 15.

It is important to note that the construction and arrangement of the orthopaedic device as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosure herein. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes and omissions may be made in the design, operating conditions and arrangement of the exemplary embodiments.

What is claimed is:

1. An orthopaedic device for realigning bone segments, comprising:
    a first attachment member, the first attachment member including:
        a clamp configured to attach to at least one of a rib bone, a transverse process, and lamina of a vertebra, the clamp including an upper arm, a lower arm, and a hinge; and
        a screw configured to be inserted into an opening in the clamp, the screw including a screw head, wherein the screw has a longitudinal axis that extends along a length of the screw and wherein the screw is configured to fix into the at least one of the rib bone, the transverse process, and the lamina of the vertebra to prevent rotational movement or sliding of the clamp along the at least one of the rib bone, the transverse process and the lamina of the vertebra; and
        a projection between shoulders of the clamp and the screw head, the projection including a second opening positioned in the projection that is configured to receive a spacer member to connect the first attachment member to a second attachment member and that is configured to retain the spacer in a direction substantially orthogonal to the longitudinal axis from the first attachment member to the second attachment member, the second opening extending from a first side of the projection to a second side of the projection in the direction substantially orthogonal to the longitudinal axis.

2. The orthopaedic device of claim 1, wherein the spacer member extends generally vertically between the first and second attachment members.

3. The orthopaedic device of claim 1, wherein the screw head includes the projection.

4. The orthopaedic device of claim 3, wherein the screw head projection comprises a U-shaped body with the second opening that comprises a slot that is configured to receive the spacer member.

5. The orthopaedic device of claim 4, wherein the U-shaped body includes a set screw configured to fix the spacer member in the slot.

6. The orthopaedic device of claim 3, wherein the screw head projection comprises a cylindrical body that includes the second opening that comprises a slot, the slot is configured to receive the spacer member.

7. The orthopaedic device of claim 6, wherein the cylindrical body includes at least one notch, and wherein the screw head is configured to break at the at least one notch to remove excess screw head above the at least one notch after insertion of the spacer member in the slot.

8. The orthopaedic device of claim 6, wherein the slot includes internal threads for receiving a set screw, the set screw is configured to fix the spacer member in the slot.

9. The orthopaedic device of claim 1, wherein the projection includes a U-shaped portion that includes the second opening, the opening is configured to receive the spacer member.

10. The orthopaedic device of claim 9, wherein the U-shaped portion includes a hole configured to receive a set screw, the set screw is configured to fix the spacer member in the U-shaped portion.

11. The orthopaedic device of claim 1, wherein the projection is an extension of the hinge.

12. The orthopaedic device of claim 1, wherein the projection includes a projection body positioned between shoulders of the clamp and the screw head to couple the projection to the first attachment member.

13. The orthopaedic device of claim 1, wherein the screw head includes a recess that extends through a length of the screw to form a cannula for the screw.

14. The orthopaedic device of claim 1, wherein the first attachment member includes a block positioned between the upper arm and lower arm and connected to the hinge, wherein the block includes an opening configured to receive the screw.

15. The orthopaedic device of claim 1, wherein the screw head includes a flat shape.

16. The orthopaedic device of claim 1, wherein the screw head includes a spherical shape.

17. The orthopaedic device of claim 1, wherein the screw head includes a recess for insertion of a tool.

18. The orthopaedic device of claim 1, wherein the clamp includes a plurality of hinges.

19. An orthopaedic device for realigning bone segments, comprising:
    an attachment member, the attachment member including:
        a clamp configured to attach to at least one of a rib bone, transverse process and lamina of a vertebra, the clamp including an upper clamp body having at least one first clamp arm, a lower clamp body having at least one second clamp arm, and a hinge; and
        a screw configured to be inserted into an opening in the clamp, the screw including a screw head, wherein the screw is configured to fix into the at least one of the rib bone, transverse process and lamina to prevent rotational movement or sliding of the clamp along the at least one of bone, transverse process and lamina,
        wherein (a) at least one of the at least one first clamp arm of the upper clamp body and the at least one second clamp arm of the lower clamp body includes a plurality of clamp arms having at least one clamp arm that is asymmetrical with respect to another clamp arm in the plurality of clamp arms; and (b) the upper clamp body is asymmetrical with respect to the lower clamp body,
        wherein the upper clamp body includes an upper shoulder and the lower clamp body includes a lower shoulder, and
        wherein the lower shoulder includes a shoulder height greater than a shoulder height of the upper shoulder, such that the lower clamp body is configured to rotate to a closed position prior to the upper clamp body rotating to a closed position upon fixing of the screw through the clamp.

20. The orthopaedic device of claim 19, wherein the upper clamp body has a length different from a length of the lower clamp body.

21. The orthopaedic device of claim 19, wherein the at least one first clamp arm is rotatable about the hinge, and wherein the at least one second clamp arm is non-rotatable about the hinge.

22. The orthopaedic device of claim 21, wherein the screw head includes a flange, and wherein when the screw is inserted into the clamp, the flange is non-perpendicular to the at least one second clamp arm.

23. The orthopaedic device of claim 19, wherein the clamp comprises one of a porous bone ingrowth surface and a porous bone ingrowth coating.

24. The orthopaedic device of claim 19, wherein the screw head includes a screw head projection.

25. The orthopaedic device of claim 24, wherein the screw head projection comprises a U-shaped body with a slot that is configured to receive a spacer member.

26. The orthopaedic device of claim 25, wherein the U-shaped body includes a set screw configured to fix the spacer member in the slot.

27. The orthopaedic device of claim 24, wherein the screw head projection comprises a cylindrical body that includes a slot, the slot is configured to receive a spacer member.

28. The orthopaedic device of claim 27, wherein the cylindrical body includes at least one notch, and wherein the screw head is configured to break at the at least one notch to remove excess screw head above the at least one notch after insertion of the spacer member in the slot.

29. The orthopaedic device of claim 27, wherein the slot includes internal threads for receiving a set screw, the set screw is configured to fix a spacer member in the slot.

30. The orthopaedic device of claim 19, further comprising a projection extending from the hinge.

31. The orthopaedic device of claim 19, wherein the screw head includes a recess that extends through a length of the screw to form a cannula for the screw.

32. The orthopaedic device of claim 19, wherein the screw head includes a flat shape.

33. The orthopaedic device of claim 19, wherein the screw head includes a spherical shape.

34. The orthopaedic device of claim 19, wherein the screw head includes a recess for insertion of a tool.

* * * * *